United States Patent
Romo et al.

(10) Patent No.: US 11,000,439 B2
(45) Date of Patent: May 11, 2021

(54) BODY INTERFACE

(71) Applicant: Ossur Iceland ehf, Reykjavik (IS)

(72) Inventors: Harry Duane Romo, Foothill Ranch, CA (US); Helga Run Palsdottir, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 238 days.

(21) Appl. No.: 16/146,455

(22) Filed: Sep. 28, 2018

(65) Prior Publication Data

US 2019/0091094 A1    Mar. 28, 2019

Related U.S. Application Data

(60) Provisional application No. 62/564,798, filed on Sep. 28, 2017.

(51) Int. Cl.
*A61H 3/00* (2006.01)
*A61H 1/02* (2006.01)
(Continued)

(52) U.S. Cl.
CPC .............. *A61H 3/00* (2013.01); *A61F 5/028* (2013.01); *A61H 1/0244* (2013.01);
(Continued)

(58) Field of Classification Search
CPC .. A61H 3/00; A61H 1/0244; A61H 2003/007; A61H 2201/1652;
(Continued)

(56) References Cited

U.S. PATENT DOCUMENTS

| 7,916 A | 1/1851 | Knapp |
| 61,487 A | 1/1867 | Vollschwitz |

(Continued)

FOREIGN PATENT DOCUMENTS

| AU | 2010271020 A1 | 2/2012 |
| AU | 2010271020 A2 | 2/2012 |

(Continued)

OTHER PUBLICATIONS

International Search Report from PCT Application No. PCT/US2018/053303, dated Dec. 21, 2018.

(Continued)

*Primary Examiner* — Kendra D Carter
*Assistant Examiner* — Arielle Wolff
(74) *Attorney, Agent, or Firm* — Workman Nydegger

(57) ABSTRACT

A body interface comprises a panel, and a lumbar support and may be configured to attach to an exoskeleton such as a leg/hip assist mechanism. The body interface has an adjustable tension provided by either a tensioning device or by the properties of materials in the panel and the lumbar support. Tension in the body interface allows the lumbar support to comfortably and dynamically contact a user's body while the panel cooperates with the leg/hip assist mechanism. First and second arms may extend from lateral portions of the panel to define with first and second belt members a circumference around the user.

18 Claims, 10 Drawing Sheets

(51) Int. Cl.
*B25J 9/00* (2006.01)
*A61F 5/02* (2006.01)

(52) U.S. Cl.
CPC ....... *B25J 9/0006* (2013.01); *A61H 2003/007* (2013.01); *A61H 2201/1626* (2013.01); *A61H 2201/1642* (2013.01); *A61H 2201/1645* (2013.01); *A61H 2201/1652* (2013.01)

(58) Field of Classification Search
CPC .... A61H 2201/1642; A61H 2201/1645; A61H 2201/1626; B25J 9/0006; A61F 5/028; A61F 5/02; A61F 5/026; A41F 9/00; A41F 9/02; A41F 9/025
See application file for complete search history.

(56) References Cited

U.S. PATENT DOCUMENTS

| | | |
|---|---|---|
| 181,948 A | 9/1876 | Kleinschuster |
| 232,420 A | 9/1880 | Smith |
| 321,145 A | 6/1885 | Spencer |
| 321,146 A | 6/1885 | Spencer |
| 328,638 A | 10/1885 | Battershall |
| 368,699 A | 8/1887 | Zervas |
| 386,642 A | 7/1888 | Mann |
| 507,172 A | 10/1893 | Shelden |
| 571,749 A | 11/1896 | Colton |
| 596,849 A | 1/1898 | Combier |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 746,563 A | 12/1903 | McMahon |
| 772,926 A | 10/1904 | Colton |
| 787,894 A | 4/1905 | Colton |
| 888,490 A | 5/1908 | Haas |
| 894,066 A | 7/1908 | Scapra |
| 980,457 A | 1/1911 | Toles |
| 1,124,596 A | 1/1915 | Dalpe |
| 1,316,915 A | 9/1919 | Meyer et al. |
| 1,393,188 A | 10/1921 | Whiteman |
| 1,463,579 A | 7/1923 | Funck |
| 1,469,661 A | 10/1923 | Migita |
| 1,481,903 A | 1/1924 | Hart |
| 1,530,713 A | 3/1925 | Clark |
| 1,558,661 A | 10/1925 | Yeganian |
| 1,607,032 A | 11/1926 | Whitley |
| 1,755,641 A | 4/1930 | Foulke |
| 1,948,785 A | 2/1934 | Dondelinger |
| 1,981,157 A | 11/1934 | Walter |
| 2,036,484 A | 4/1936 | Le May |
| 2,100,964 A | 11/1937 | Kendrick |
| 2,117,309 A | 5/1938 | Fritsch |
| 2,219,475 A | 10/1940 | Flaherty |
| 2,409,381 A | 10/1946 | Pease, Jr. |
| 2,543,370 A | 2/1951 | Kludt et al. |
| 2,554,337 A | 5/1951 | Lampert |
| 2,630,801 A | 3/1953 | Mest et al. |
| 2,696,011 A | 12/1954 | Galdik |
| 2,749,550 A | 6/1956 | Pease |
| 2,775,767 A | 1/1957 | Gould |
| 2,793,368 A | 5/1957 | Nouel |
| 2,808,050 A | 10/1957 | Ward |
| 2,815,021 A | 12/1957 | Freeman |
| 2,828,737 A | 4/1958 | Hale |
| 2,904,040 A | 9/1959 | Hale |
| 2,906,260 A | 9/1959 | Myers |
| 2,906,261 A | 9/1959 | Craig |
| 3,095,875 A | 7/1963 | Davidson et al. |
| 3,096,760 A | 7/1963 | Nelkin |
| 3,128,514 A | 4/1964 | Parker et al. |
| 3,274,996 A | 9/1966 | Jewett |
| 3,282,264 A | 11/1966 | Connelly |
| 3,351,053 A | 11/1967 | Stuttle |
| 3,358,678 A | 12/1967 | Kultsar |
| 3,371,351 A | 3/1968 | Allain |
| 3,434,469 A | 3/1969 | Swift |
| 3,449,769 A | 6/1969 | Mizen |
| 3,480,012 A | 11/1969 | Smithers et al. |
| 3,509,875 A | 5/1970 | Richter |
| 3,548,817 A | 12/1970 | Mittasch |
| 3,563,431 A | 2/1971 | Pletz |
| 3,570,480 A | 3/1971 | Stubbs |
| 3,578,773 A | 5/1971 | Schultz |
| 3,600,717 A | 8/1971 | McKeehan |
| 3,601,819 A | 8/1971 | Herrmann |
| 3,603,316 A | 9/1971 | Lehman |
| 3,762,421 A | 10/1973 | Sax, Sr. |
| 3,771,513 A | 11/1973 | Velazquez |
| 3,793,749 A | 2/1974 | Gertsch et al. |
| 3,808,644 A | 5/1974 | Schoch |
| 3,812,850 A | 5/1974 | Reiman |
| 3,816,211 A | 6/1974 | Haigh |
| 3,834,048 A | 9/1974 | Maurer |
| 3,889,664 A | 6/1975 | Heuser et al. |
| 3,902,503 A | 9/1975 | Gaylord, Jr. |
| 3,920,008 A | 11/1975 | Lehman |
| 3,926,182 A | 12/1975 | Stabholz |
| 3,927,665 A | 12/1975 | Wax |
| 3,945,376 A | 3/1976 | Kuehnegger |
| 4,042,433 A | 8/1977 | Hardy et al. |
| 4,055,168 A | 10/1977 | Miller et al. |
| 4,071,387 A | 1/1978 | Schlaepfer |
| 4,099,524 A | 7/1978 | Cueman et al. |
| 4,114,788 A | 9/1978 | Zufich |
| 4,162,672 A | 7/1979 | Yazaki |
| 4,173,973 A | 11/1979 | Hendricks |
| 4,175,553 A | 11/1979 | Rosenberg |
| 4,180,870 A | 1/1980 | Radulovic et al. |
| 4,182,338 A | 1/1980 | Stanulis |
| 4,230,101 A | 10/1980 | Gold |
| 4,261,081 A | 4/1981 | Lott |
| 4,285,336 A | 8/1981 | Oebser et al. |
| 4,298,149 A | 11/1981 | Gottschalk et al. |
| 4,308,861 A | 1/1982 | Kelly |
| 4,322,092 A | 3/1982 | Feucht et al. |
| 4,383,523 A | 5/1983 | Schurman |
| 4,392,489 A | 7/1983 | Wagner, Sr. |
| 4,433,456 A | 2/1984 | Baggio |
| RE31,564 E | 4/1984 | Hendricks |
| 4,475,543 A | 10/1984 | Brooks et al. |
| 4,479,495 A | 10/1984 | Isaacson |
| 4,494,536 A | 1/1985 | Latenser |
| 4,502,471 A | 3/1985 | Owens |
| 4,508,110 A | 4/1985 | Modglin |
| 4,531,515 A | 7/1985 | Rolfes |
| 4,555,830 A | 12/1985 | Petrini et al. |
| 4,559,933 A | 12/1985 | Batard et al. |
| 4,569,336 A | 2/1986 | Wheeler |
| 4,574,500 A | 3/1986 | Aldinio et al. |
| 4,574,789 A | 3/1986 | Forster |
| 4,574,790 A | 3/1986 | Wellershaus |
| 4,590,939 A | 5/1986 | Sakowski |
| 4,608,971 A | 9/1986 | Borschneck |
| 4,616,524 A | 10/1986 | Bidoia |
| 4,619,657 A | 10/1986 | Keates et al. |
| 4,628,913 A | 12/1986 | Lerman |
| 4,631,839 A | 12/1986 | Bonetti et al. |
| 4,631,840 A | 12/1986 | Gamm |
| 4,635,626 A | 1/1987 | Lerman |
| 4,640,269 A | 2/1987 | Goins |
| 4,648,390 A | 3/1987 | Friddle |
| 4,649,574 A | 3/1987 | Michels |
| 4,654,985 A | 4/1987 | Chalmers |
| 4,655,201 A | 4/1987 | Pirmantgen |
| 4,658,807 A | 4/1987 | Swain |
| 4,660,302 A | 4/1987 | Arieh et al. |
| 4,669,451 A | 6/1987 | Blauth et al. |
| 4,677,699 A | 7/1987 | Barabe |
| 4,677,969 A | 7/1987 | Calabrese |
| 4,680,878 A | 7/1987 | Pozzobon et al. |

(56) References Cited

U.S. PATENT DOCUMENTS

| | | |
|---|---|---|
| 4,691,696 A | 9/1987 | Farfan De Los Godos |
| 4,696,291 A | 9/1987 | Tyo |
| 4,697,583 A | 10/1987 | Mason et al. |
| 4,697,592 A | 10/1987 | Maddux et al. |
| 4,716,898 A | 1/1988 | Chauve et al. |
| 4,719,670 A | 1/1988 | Kurt |
| 4,719,709 A | 1/1988 | Vaccari |
| 4,761,834 A | 8/1988 | Kolb |
| 4,796,610 A | 1/1989 | Cromartie |
| 4,799,297 A | 1/1989 | Baggio et al. |
| 4,802,291 A | 2/1989 | Sartor |
| 4,805,605 A | 2/1989 | Glassman |
| 4,807,605 A | 2/1989 | Mattingly |
| 4,811,503 A | 3/1989 | Iwama |
| 4,836,195 A | 6/1989 | Berrehail |
| 4,843,688 A | 7/1989 | Ikeda |
| 4,862,878 A | 9/1989 | Davison et al. |
| 4,870,761 A | 10/1989 | Tracy |
| 4,896,660 A | 1/1990 | Scott |
| 4,905,678 A | 3/1990 | Cumins et al. |
| 4,923,474 A | 5/1990 | Klasson et al. |
| 4,937,952 A | 7/1990 | Olivieri |
| 4,961,544 A | 10/1990 | Bidoia |
| 4,963,208 A | 10/1990 | Muncy et al. |
| 4,976,257 A | 12/1990 | Akin et al. |
| 4,986,263 A | 1/1991 | Dickerson et al. |
| 4,997,438 A | 3/1991 | Nipper |
| 5,027,482 A | 7/1991 | Torppey |
| 5,072,725 A | 12/1991 | Miller |
| 5,074,288 A | 12/1991 | Miller |
| 5,092,321 A | 3/1992 | Spademan |
| 5,098,770 A | 3/1992 | Paire |
| 5,105,828 A | 4/1992 | Grant |
| 5,111,807 A | 5/1992 | Spann et al. |
| 5,117,567 A | 6/1992 | Berger |
| 5,120,288 A | 6/1992 | Sinaki |
| 5,121,741 A | 6/1992 | Bremer et al. |
| 5,127,897 A | 7/1992 | Roller |
| 5,135,470 A | 8/1992 | Reeves |
| 5,135,471 A | 8/1992 | Houswerth |
| 5,154,690 A | 10/1992 | Shiono |
| 5,157,813 A | 10/1992 | Carroll |
| 5,170,505 A | 12/1992 | Rohrer |
| 5,171,296 A | 12/1992 | Herman |
| 5,176,131 A | 1/1993 | Votel et al. |
| 5,177,882 A | 1/1993 | Berger |
| 5,181,331 A | 1/1993 | Berger |
| 5,183,036 A | 2/1993 | Spademan |
| D334,063 S | 3/1993 | Dewall |
| 5,199,940 A | 4/1993 | Morris et al. |
| 5,201,074 A | 4/1993 | Dicker |
| 5,203,765 A | 4/1993 | Friddle, Jr. |
| 5,215,518 A | 6/1993 | Rosen |
| 5,226,874 A | 7/1993 | Heinz et al. |
| 5,230,698 A | 7/1993 | Garth |
| 5,259,831 A | 11/1993 | Lebron |
| 5,259,833 A | 11/1993 | Barnett |
| 5,267,928 A | 12/1993 | Barile et al. |
| 5,282,460 A | 2/1994 | Boldt |
| 5,295,947 A | 3/1994 | Muncy |
| 5,295,996 A | 3/1994 | Blair |
| 5,307,521 A | 5/1994 | Davis |
| 5,313,952 A | 5/1994 | Hoch |
| 5,318,575 A | 6/1994 | Chesterfield et al. |
| 5,327,662 A | 7/1994 | Hallenbeck |
| 5,334,135 A | 8/1994 | Grim et al. |
| 5,342,289 A | 8/1994 | Munny |
| 5,346,461 A | 9/1994 | Heinz et al. |
| 5,362,304 A | 11/1994 | Varn |
| 5,363,863 A | 11/1994 | Lelli et al. |
| 5,365,947 A | 11/1994 | Bonutti |
| 5,368,552 A | 11/1994 | Williamson et al. |
| 5,376,129 A | 12/1994 | Faulkner et al. |
| 5,383,893 A | 1/1995 | Daneshvar |
| 5,385,536 A | 1/1995 | Burkhead et al. |
| 5,387,245 A | 2/1995 | Fay et al. |
| 5,399,151 A | 3/1995 | Smith |
| 5,407,420 A | 4/1995 | Bastyr et al. |
| 5,421,809 A | 6/1995 | Rise |
| 5,423,852 A | 6/1995 | Daneshvar |
| 5,429,587 A | 7/1995 | Gates |
| 5,433,648 A | 7/1995 | Frydman |
| 5,433,697 A | 7/1995 | Cox |
| 5,435,015 A | 7/1995 | Ellis-Brewer |
| 5,437,614 A | 8/1995 | Grim |
| 5,437,617 A | 8/1995 | Heinz et al. |
| 5,437,619 A | 8/1995 | Malewicz et al. |
| 5,449,338 A | 9/1995 | Trudell |
| 5,450,858 A | 9/1995 | Zablotsky et al. |
| 5,466,214 A | 11/1995 | Calderon-Garciduenas |
| 5,484,395 A | 1/1996 | Deroche |
| 5,499,965 A | 3/1996 | Sanchez |
| 5,500,959 A | 3/1996 | Yewer, Jr. |
| 5,502,902 A | 4/1996 | Sussmann |
| 5,503,314 A | 4/1996 | Fiscus |
| 5,503,620 A | 4/1996 | Danzger |
| 5,507,681 A | 4/1996 | Smith et al. |
| 5,507,834 A | 4/1996 | Laghi |
| 5,520,619 A | 5/1996 | Martin |
| 5,522,792 A | 6/1996 | Bassett et al. |
| 5,531,669 A | 7/1996 | Varnau |
| 5,536,246 A | 7/1996 | Saunders |
| 5,539,020 A | 7/1996 | Bracken et al. |
| 5,548,843 A | 8/1996 | Chase et al. |
| 5,551,950 A | 9/1996 | Oppen |
| 5,556,374 A | 9/1996 | Grace et al. |
| 5,558,628 A | 9/1996 | Bzoch |
| 5,569,171 A | 10/1996 | Muncy |
| 5,571,355 A | 11/1996 | Kornylo |
| 5,599,287 A | 2/1997 | Beczak, Sr. et al. |
| 5,599,288 A | 2/1997 | Shirley et al. |
| 5,603,122 A | 2/1997 | Kania |
| 5,620,412 A | 4/1997 | Modglin |
| 5,622,529 A | 4/1997 | Calabrese |
| 5,632,724 A | 5/1997 | Lerman et al. |
| 5,634,891 A | 6/1997 | Beczak, Sr. et al. |
| 5,638,588 A | 6/1997 | Jungkind |
| 5,669,116 A | 9/1997 | Jungkind |
| 5,674,187 A | 10/1997 | Zepf |
| 5,681,270 A | 10/1997 | Klearman et al. |
| 5,685,830 A | 11/1997 | Bonutti |
| 5,685,831 A | 11/1997 | Floyd |
| 5,688,137 A | 11/1997 | Bustance |
| 5,690,260 A | 11/1997 | Aikins et al. |
| 5,690,609 A | 11/1997 | Heinze, III |
| 5,695,452 A | 12/1997 | Grim et al. |
| 5,695,520 A | 12/1997 | Bruckner et al. |
| 5,704,904 A | 1/1998 | Dunfee |
| 5,704,937 A | 1/1998 | Martin |
| 5,708,977 A | 1/1998 | Morkunas |
| 5,718,670 A | 2/1998 | Bremer |
| 5,722,940 A | 3/1998 | Gaylord, Jr. et al. |
| 5,724,993 A | 3/1998 | Dunfee |
| 5,725,139 A | 3/1998 | Smith |
| 5,728,054 A | 3/1998 | Martin |
| 5,728,168 A | 3/1998 | Laghi et al. |
| 5,732,483 A | 3/1998 | Cagliari |
| 5,735,807 A | 4/1998 | Cropper |
| 5,737,854 A | 4/1998 | Sussmann |
| 5,746,218 A | 5/1998 | Edge |
| 5,752,640 A | 5/1998 | Proulx |
| 5,778,565 A | 7/1998 | Holt et al. |
| 5,782,782 A | 7/1998 | Miller |
| 5,795,316 A | 8/1998 | Gaylord |
| RE35,940 E | 10/1998 | Heinz et al. |
| 5,816,251 A | 10/1998 | Glisan |
| 5,819,378 A | 10/1998 | Doyle |
| 5,823,981 A | 10/1998 | Grim et al. |
| 5,826,766 A | 10/1998 | Aftanas |
| 5,827,211 A | 10/1998 | Sellinger |
| 5,830,167 A | 11/1998 | Jung |
| 5,836,493 A | 11/1998 | Grunsted et al. |
| 5,840,050 A | 11/1998 | Lerman |
| 5,848,979 A | 12/1998 | Bonutti et al. |

(56) References Cited

U.S. PATENT DOCUMENTS

| | | |
|---|---|---|
| 5,853,378 A | 12/1998 | Modglin |
| 5,853,379 A | 12/1998 | Ostojic |
| 5,857,988 A | 1/1999 | Shirley |
| 5,868,292 A | 2/1999 | Stephens et al. |
| 5,890,640 A | 4/1999 | Thompson |
| 5,891,061 A | 4/1999 | Kaiser |
| 5,893,871 A | 4/1999 | Tanaka |
| 5,911,697 A | 6/1999 | Biedermann et al. |
| 5,916,070 A | 6/1999 | Donohue |
| 5,938,629 A | 8/1999 | Bloedau |
| 5,950,628 A | 9/1999 | Dunfee |
| 5,954,250 A | 9/1999 | Hall et al. |
| 5,954,253 A | 9/1999 | Swetish |
| 5,967,998 A | 10/1999 | Modglin |
| 5,968,002 A | 10/1999 | Morrisseau |
| 5,993,403 A | 11/1999 | Martin |
| 6,007,503 A | 12/1999 | Berger et al. |
| 6,010,472 A | 1/2000 | Schiller |
| 6,027,466 A | 2/2000 | Diefenbacher et al. |
| 6,029,273 A | 2/2000 | McCrane |
| 6,036,664 A | 3/2000 | Martin, Sr. et al. |
| 6,039,707 A | 3/2000 | Crawford et al. |
| 6,063,047 A | 5/2000 | Minne |
| 6,066,108 A | 5/2000 | Lundberg |
| 6,070,776 A | 6/2000 | Furnary et al. |
| 6,090,057 A | 7/2000 | Collins et al. |
| 6,099,490 A | 8/2000 | Turtzo |
| 6,110,138 A | 8/2000 | Shirley |
| 6,113,562 A | 9/2000 | Bonutti et al. |
| 6,117,096 A | 9/2000 | Hassard |
| RE36,905 E | 10/2000 | Noble et al. |
| 6,125,792 A | 10/2000 | Gee |
| 6,129,638 A | 10/2000 | Davis |
| 6,129,691 A | 10/2000 | Ruppert |
| 6,156,001 A | 12/2000 | Frangi et al. |
| 6,159,248 A | 12/2000 | Gramnas |
| 6,182,288 B1 | 2/2001 | Kibbee |
| 6,189,538 B1 | 2/2001 | Thorpe |
| 6,190,343 B1 | 2/2001 | Heinz et al. |
| D438,624 S | 3/2001 | Reina |
| 6,206,932 B1 | 3/2001 | Johnson |
| 6,213,968 B1 | 4/2001 | Heinz et al. |
| 6,227,937 B1 | 5/2001 | Principe |
| 6,245,033 B1 | 6/2001 | Martin |
| 6,254,561 B1 | 7/2001 | Borden |
| 6,256,798 B1 | 7/2001 | Egolf et al. |
| 6,267,390 B1 | 7/2001 | Maravetz et al. |
| 6,267,741 B1 | 7/2001 | Lerman |
| 6,282,729 B1 | 9/2001 | Oikawa et al. |
| 6,289,558 B1 | 9/2001 | Hammerslag |
| 6,301,526 B1 | 10/2001 | Kim et al. |
| 6,315,746 B1 | 11/2001 | Garth et al. |
| 6,322,529 B1 | 11/2001 | Chung |
| 6,325,023 B1 | 12/2001 | Elnatan |
| 6,338,723 B1 | 1/2002 | Carpenter et al. |
| 6,401,786 B1 | 6/2002 | Tedeschi et al. |
| 6,413,232 B1 | 7/2002 | Townsend et al. |
| 6,416,074 B1 | 7/2002 | Maravetz et al. |
| 6,419,652 B1 | 7/2002 | Slautterback |
| 6,425,876 B1 | 7/2002 | Frangi et al. |
| 6,428,493 B1 | 8/2002 | Pior et al. |
| 6,432,073 B2 | 8/2002 | Pior et al. |
| 6,471,665 B1 | 10/2002 | Milbourn et al. |
| 6,478,759 B1 | 11/2002 | Modglin et al. |
| 6,494,853 B1 | 12/2002 | Rossi et al. |
| 6,502,577 B1 | 1/2003 | Bonutti |
| 6,503,213 B2 | 1/2003 | Bonutti |
| 6,508,776 B2 | 1/2003 | Chiang et al. |
| 6,517,502 B2 | 2/2003 | Heyman et al. |
| 6,540,703 B1 | 4/2003 | Lerman |
| 6,589,195 B1 | 7/2003 | Schwenn et al. |
| 6,599,263 B1 | 7/2003 | Bonutti et al. |
| 6,602,214 B2 | 8/2003 | Heinz et al. |
| 6,605,052 B1 | 8/2003 | Cool et al. |
| 6,609,642 B2 | 8/2003 | Heinz et al. |
| 6,623,419 B1 | 9/2003 | Smith et al. |
| 6,652,596 B2 | 11/2003 | Smith et al. |
| 6,656,144 B1 | 12/2003 | Coligado |
| 6,676,617 B1 | 1/2004 | Miller |
| 6,676,620 B2 | 1/2004 | Schwenn et al. |
| 6,685,662 B1 | 2/2004 | Curry et al. |
| 6,688,943 B2 | 2/2004 | Nagaoka |
| 6,689,080 B2 | 2/2004 | Castillo |
| 6,702,770 B2 | 3/2004 | Bremer et al. |
| 6,711,750 B1 | 3/2004 | Yoo |
| 6,711,787 B2 | 3/2004 | Jungkind et al. |
| 6,726,641 B2 | 4/2004 | Chiang et al. |
| 6,726,643 B1 | 4/2004 | Martin |
| 6,769,155 B2 | 8/2004 | Hess et al. |
| 6,770,047 B2 | 8/2004 | Bonutti |
| 6,773,411 B1 | 8/2004 | Alvarez |
| 6,790,191 B1 | 9/2004 | Hendricks |
| 6,802,442 B1 | 10/2004 | Thompson |
| D499,806 S | 12/2004 | Machin et al. |
| 6,827,653 B2 | 12/2004 | Be |
| D501,078 S | 1/2005 | Cabana |
| 6,893,098 B2 | 5/2005 | Kohani |
| 6,893,411 B1 | 5/2005 | Modglin |
| 6,913,585 B2 | 7/2005 | Salmon et al. |
| 6,921,375 B2 | 7/2005 | Kihara |
| 6,921,377 B2 | 7/2005 | Bonutti |
| 6,923,780 B2 | 8/2005 | Price et al. |
| 6,926,685 B1 | 8/2005 | Modglin |
| 6,929,616 B2 | 8/2005 | Bonutti et al. |
| 6,936,021 B1 | 8/2005 | Smith |
| 6,942,630 B2 | 9/2005 | Behan |
| 6,951,547 B1 | 10/2005 | Park et al. |
| 6,962,572 B1 | 11/2005 | Zahiri |
| 6,964,644 B1 | 11/2005 | Garth |
| 6,991,611 B2 | 1/2006 | Rhee |
| 7,001,348 B2 | 2/2006 | Garth et al. |
| 7,001,350 B2 | 2/2006 | Grosso |
| 7,025,737 B2 | 4/2006 | Modglin |
| 7,028,873 B1 | 4/2006 | Collier et al. |
| 7,034,251 B1 | 4/2006 | Child et al. |
| 7,048,707 B2 | 5/2006 | Schwenn et al. |
| 7,074,204 B2 | 7/2006 | Fujii et al. |
| 7,083,584 B2 | 8/2006 | Coligado |
| 7,083,585 B2 | 8/2006 | Latham |
| 7,087,032 B1 | 8/2006 | Ikeda |
| 7,101,348 B2 | 9/2006 | Garth |
| 7,118,543 B2 | 10/2006 | Telles et al. |
| 7,128,724 B2 | 10/2006 | Marsh |
| 7,134,224 B2 | 11/2006 | Elkington et al. |
| 7,137,973 B2 | 11/2006 | Plauche et al. |
| 7,140,691 B2 | 11/2006 | Kohani |
| 7,166,083 B2 | 1/2007 | Bledsoe |
| 7,186,229 B2 | 3/2007 | Schwenn et al. |
| 7,198,610 B2 | 4/2007 | Ingimundarson et al. |
| 7,201,727 B2 | 4/2007 | Schwenn et al. |
| 7,235,059 B2 | 6/2007 | Mason et al. |
| 7,281,341 B2 | 10/2007 | Reagan et al. |
| 7,306,571 B2 | 12/2007 | Schwenn et al. |
| 7,306,573 B2 | 12/2007 | Bonutti |
| 7,309,304 B2 | 12/2007 | Stewart et al. |
| 7,316,660 B1 | 1/2008 | Modglin |
| 7,320,670 B1 | 1/2008 | Modglin |
| 7,322,950 B2 | 1/2008 | Modglin |
| 7,329,231 B2 | 2/2008 | Frank |
| 7,331,126 B2 | 2/2008 | Johnson |
| 7,351,368 B2 | 4/2008 | Abrams |
| 7,389,547 B1 | 6/2008 | Wiens |
| 7,402,147 B1 | 7/2008 | Allen |
| 7,404,804 B2 | 7/2008 | Bonutti |
| 7,410,338 B2 | 8/2008 | Schiele et al. |
| 7,413,554 B2 | 8/2008 | Kobayashi et al. |
| 7,416,565 B1 | 8/2008 | Al-Turaikl |
| 7,438,698 B2 | 10/2008 | Daiju |
| 7,473,235 B2 | 1/2009 | Schwenn et al. |
| 7,476,185 B2 | 1/2009 | Drennan |
| 7,513,018 B2 | 4/2009 | Koenig et al. |
| 7,549,970 B2 | 6/2009 | Tweardy |
| 7,578,798 B2 | 8/2009 | Rhee |
| 7,591,050 B2 | 9/2009 | Hammerslag |

(56) References Cited

U.S. PATENT DOCUMENTS

| | | |
|---|---|---|
| 7,597,671 B2 | 10/2009 | Baumgartner et al. |
| 7,597,672 B2 | 10/2009 | Kruijsen et al. |
| 7,600,660 B2 | 10/2009 | Kasper et al. |
| 7,615,021 B2 | 11/2009 | Nordt, III et al. |
| 7,618,386 B2 | 11/2009 | Nordt, III et al. |
| 7,618,389 B2 | 11/2009 | Nordt, III et al. |
| 7,654,972 B2 | 2/2010 | Alleyne |
| 7,662,121 B2 | 2/2010 | Zours |
| 7,670,306 B2 | 3/2010 | Nordt, III et al. |
| 7,682,219 B2 | 3/2010 | Falla |
| 7,699,797 B2 | 4/2010 | Nordt, III et al. |
| 7,704,219 B2 | 4/2010 | Nordt, III et al. |
| 7,727,048 B2 | 6/2010 | Gransberry |
| 7,727,174 B2 | 6/2010 | Chang et al. |
| 7,757,307 B2 | 7/2010 | Wong |
| 7,775,999 B2 | 8/2010 | Brown |
| 7,806,842 B2 | 10/2010 | Stevenson et al. |
| 7,815,585 B2 | 10/2010 | Vollbrecht |
| 7,819,831 B2 | 10/2010 | Dellanno |
| 7,833,182 B2 | 11/2010 | Hughes |
| 7,842,000 B2 | 11/2010 | Lai et al. |
| 7,857,776 B2 | 12/2010 | Frisbie |
| 7,862,524 B2 | 1/2011 | Carignan et al. |
| 7,862,529 B2 | 1/2011 | Brown |
| 7,862,621 B2 | 1/2011 | Kloos et al. |
| 7,871,388 B2 | 1/2011 | Brown |
| 7,878,998 B2 | 2/2011 | Nordt, III et al. |
| 7,887,500 B2 | 2/2011 | Nordt, III et al. |
| 7,914,473 B2 | 3/2011 | Josey |
| D636,494 S | 4/2011 | Garth et al. |
| 7,922,680 B2 | 4/2011 | Nordt, III et al. |
| 7,947,004 B2 | 5/2011 | Kazerooni et al. |
| 7,950,112 B2 | 5/2011 | Hammerslag et al. |
| 7,954,204 B2 | 6/2011 | Hammerslag et al. |
| 7,955,285 B2 | 6/2011 | Bonutti et al. |
| 7,959,591 B2 | 6/2011 | Powers et al. |
| 7,993,296 B2 | 8/2011 | Nordt, III et al. |
| 8,002,724 B2 | 8/2011 | Hu et al. |
| 8,006,877 B2 | 8/2011 | Lowry et al. |
| 8,038,635 B2 | 10/2011 | Dellanno |
| 8,038,637 B2 | 10/2011 | Bonutti |
| 8,047,893 B2 | 11/2011 | Fenske |
| 8,048,014 B2 | 11/2011 | Brown |
| 8,066,161 B2 | 11/2011 | Green et al. |
| 8,066,654 B2 | 11/2011 | Sandifer et al. |
| 8,091,182 B2 | 1/2012 | Hammerslag et al. |
| 8,142,377 B2 | 3/2012 | Garth et al. |
| 8,152,699 B1 | 4/2012 | Ma et al. |
| 8,162,194 B2 | 4/2012 | Gleason |
| 8,162,864 B2 | 4/2012 | Kruijsen et al. |
| 8,172,779 B2 | 5/2012 | Ingimundarson et al. |
| 8,214,926 B2 | 7/2012 | Brown |
| 8,216,167 B2 | 7/2012 | Garth et al. |
| 8,273,043 B2 | 9/2012 | Bonutti et al. |
| 8,303,528 B2 | 11/2012 | Ingimundarson et al. |
| 8,308,669 B2 | 11/2012 | Nace |
| 8,308,670 B2 | 11/2012 | Sandifer et al. |
| 8,308,869 B2 | 11/2012 | Gardner et al. |
| 8,356,604 B2 | 1/2013 | Tweardy et al. |
| 8,372,023 B2 | 2/2013 | Garth et al. |
| 8,381,314 B2 | 2/2013 | Takamoto et al. |
| 8,409,118 B2 | 4/2013 | Agrawal et al. |
| 8,425,436 B2 | 4/2013 | Sankai |
| 8,460,222 B2 | 6/2013 | Garrec |
| 8,556,840 B2 | 10/2013 | Burke et al. |
| 8,591,442 B2 | 11/2013 | Bonutti et al. |
| 8,597,222 B2 | 12/2013 | Lucero et al. |
| 8,641,782 B2 | 2/2014 | Kim et al. |
| 8,657,769 B2 | 2/2014 | Ingimundarson et al. |
| 8,728,019 B2 | 5/2014 | Kruijsen et al. |
| 8,758,284 B1 | 6/2014 | Kozersky |
| 8,795,215 B2 | 8/2014 | Rossi |
| 8,893,312 B2 | 11/2014 | Takamoto et al. |
| 8,926,537 B2 | 1/2015 | Ingimundarson et al. |
| 8,956,315 B2 | 2/2015 | Garth et al. |
| 8,968,222 B2 | 3/2015 | Kazerooni et al. |
| 8,992,452 B2 | 3/2015 | Carter |
| 9,144,528 B2 | 9/2015 | Agrawal et al. |
| 9,155,651 B2 | 10/2015 | Ochoa |
| 9,204,730 B2 | 12/2015 | Brown |
| 9,205,017 B2 | 12/2015 | Doyle |
| 9,220,625 B2 | 12/2015 | Ingimundarson et al. |
| 9,345,606 B2 | 5/2016 | Bonutti et al. |
| 9,358,173 B2 | 6/2016 | Fu et al. |
| 9,370,440 B2 | 6/2016 | Ingimundarson et al. |
| 9,375,325 B2 | 6/2016 | Garrec et al. |
| 9,404,618 B2 | 8/2016 | Brown et al. |
| 9,414,953 B2 | 8/2016 | Ingimundarson et al. |
| 9,427,865 B2 | 8/2016 | Doyle |
| 9,468,554 B2 | 10/2016 | Petursson et al. |
| 9,504,596 B1 | 11/2016 | Kozersky |
| 9,522,077 B1 | 12/2016 | Johnson |
| 9,554,935 B2 | 1/2017 | Ingimundarson et al. |
| 9,572,705 B2 | 2/2017 | Ingimundarson et al. |
| 9,597,219 B2 | 3/2017 | Ingimundarson et al. |
| 9,636,247 B2 | 5/2017 | Miller et al. |
| 9,795,500 B2 | 10/2017 | Ingimundarson et al. |
| 9,889,554 B2 | 2/2018 | Van Engelhoven et al. |
| 2001/0020144 A1 | 9/2001 | Heinz et al. |
| 2001/0031936 A1 | 10/2001 | Pior et al. |
| 2002/0032397 A1 | 3/2002 | Coligado |
| 2002/0068890 A1 | 6/2002 | Schwenn et al. |
| 2002/0148461 A1 | 10/2002 | Heinz et al. |
| 2002/0158097 A1 | 10/2002 | Beale |
| 2002/0165474 A1 | 11/2002 | Chiang et al. |
| 2002/0165475 A1 | 11/2002 | Chiang et al. |
| 2003/0000986 A1 | 1/2003 | Smith |
| 2003/0028952 A1 | 2/2003 | Fujii et al. |
| 2003/0115954 A1 | 6/2003 | Zemlyakov et al. |
| 2003/0125650 A1 | 7/2003 | Grosso |
| 2003/0125705 A1 | 7/2003 | Ruman et al. |
| 2003/0139698 A1 | 7/2003 | Hyson |
| 2003/0220594 A1 | 11/2003 | Halvorson et al. |
| 2003/0229301 A1 | 12/2003 | Coligado |
| 2004/0024340 A1 | 2/2004 | Schwenn et al. |
| 2004/0050391 A1 | 3/2004 | Kiwala et al. |
| 2004/0082895 A1 | 4/2004 | Price et al. |
| 2004/0097857 A1 | 5/2004 | Reinecke et al. |
| 2004/0108350 A1 | 6/2004 | Warren |
| 2004/0116260 A1 | 6/2004 | Drennan |
| 2004/0132380 A1 | 7/2004 | Kihara |
| 2004/0133138 A1 | 7/2004 | Modglin |
| 2004/0143204 A1 | 7/2004 | Salmon et al. |
| 2004/0162582 A1 | 8/2004 | Banziger |
| 2004/0254505 A1 | 12/2004 | Begley et al. |
| 2005/0054960 A1 | 3/2005 | Telles et al. |
| 2005/0059917 A1 | 3/2005 | Garth et al. |
| 2005/0067816 A1 | 3/2005 | Buckman |
| 2005/0081339 A1 | 4/2005 | Sakabayashi |
| 2005/0131323 A1 | 6/2005 | Bledsoe |
| 2005/0137508 A1 | 6/2005 | Miller |
| 2005/0154337 A1 | 7/2005 | Meyer |
| 2005/0160627 A1 | 7/2005 | Dalgaard et al. |
| 2005/0165338 A1 | 7/2005 | Iglesias et al. |
| 2005/0228325 A1 | 10/2005 | Zours et al. |
| 2005/0240134 A1 | 10/2005 | Brown |
| 2005/0251074 A1 | 11/2005 | Latham |
| 2005/0267390 A1 | 12/2005 | Garth et al. |
| 2005/0273025 A1 | 12/2005 | Houser |
| 2006/0011690 A1 | 1/2006 | Bareno |
| 2006/0052733 A1 | 3/2006 | Schwenn et al. |
| 2006/0064048 A1 | 3/2006 | Stano |
| 2006/0074365 A1 | 4/2006 | Brown |
| 2006/0079821 A1 | 4/2006 | Rauch |
| 2006/0129077 A1 | 6/2006 | Parizot |
| 2006/0135900 A1 | 6/2006 | Ingimundarson et al. |
| 2006/0135901 A1 | 6/2006 | Ingimundarson et al. |
| 2006/0135903 A1 | 6/2006 | Ingimundaron et al. |
| 2006/0155229 A1 | 7/2006 | Ceriani et al. |
| 2006/0156517 A1 | 7/2006 | Hammerslag et al. |
| 2006/0206992 A1 | 9/2006 | Godshaw et al. |
| 2006/0254598 A1 | 11/2006 | Saul |
| 2006/0260620 A1 | 11/2006 | Kazerooni et al. |
| 2007/0060445 A1 | 3/2007 | Reinkensmeyer et al. |

(56) References Cited

U.S. PATENT DOCUMENTS

| | | |
|---|---|---|
| 2007/0152007 A1 | 7/2007 | Kauss et al. |
| 2007/0167895 A1 | 7/2007 | Gramza et al. |
| 2007/0179417 A1 | 8/2007 | Schwenn et al. |
| 2007/0185425 A1 | 8/2007 | Einarsson et al. |
| 2007/0225620 A1 | 9/2007 | Carignan et al. |
| 2008/0045873 A1 | 2/2008 | Zours |
| 2008/0091132 A1 | 4/2008 | Bonutti |
| 2008/0195010 A1 | 8/2008 | Lai et al. |
| 2008/0208090 A1 | 8/2008 | Vollbrecht |
| 2008/0208091 A1 | 8/2008 | Vollbrecht et al. |
| 2008/0249448 A1 | 10/2008 | Stevenson et al. |
| 2008/0262401 A1 | 10/2008 | Wagner et al. |
| 2008/0302839 A1 | 12/2008 | Murdoch et al. |
| 2008/0319362 A1 | 12/2008 | Joseph |
| 2009/0025115 A1 | 1/2009 | Duffy et al. |
| 2009/0030353 A1 | 1/2009 | Bonutti et al. |
| 2009/0030359 A1 | 1/2009 | Wikenheiser et al. |
| 2009/0062704 A1 | 3/2009 | Brown et al. |
| 2009/0082707 A1 | 3/2009 | Rumsey |
| 2009/0100649 A1 | 4/2009 | Bar et al. |
| 2009/0124948 A1 | 5/2009 | Ingimundarson et al. |
| 2009/0127308 A1 | 5/2009 | Mori et al. |
| 2009/0182253 A1 | 7/2009 | Grim et al. |
| 2009/0192425 A1 | 7/2009 | Garth et al. |
| 2009/0198166 A1 | 8/2009 | Shlomovitz |
| 2009/0275871 A1 | 11/2009 | Liu |
| 2009/0287128 A1 | 11/2009 | Ingimundarson et al. |
| 2010/0010568 A1 | 1/2010 | Brown |
| 2010/0037369 A1 | 2/2010 | Reichert |
| 2010/0139057 A1 | 6/2010 | Soderberg et al. |
| 2010/0204630 A1 | 8/2010 | Sandifer et al. |
| 2010/0204804 A1 | 8/2010 | Garrec |
| 2010/0205713 A1 | 8/2010 | Takamoto et al. |
| 2010/0217163 A1 | 8/2010 | Sankai |
| 2010/0217167 A1 | 8/2010 | Ingimundarson et al. |
| 2010/0228170 A1 | 9/2010 | Imai |
| 2010/0256717 A1 | 10/2010 | Brown |
| 2010/0268139 A1 | 10/2010 | Garth |
| 2010/0268141 A1 | 10/2010 | Bannister |
| 2010/0274364 A1 | 10/2010 | Pacanowsky et al. |
| 2010/0292622 A1 | 11/2010 | Weissleder et al. |
| 2010/0299959 A1 | 12/2010 | Hammerslag et al. |
| 2010/0318010 A1 | 12/2010 | Sandifer et al. |
| 2011/0000005 A1 | 1/2011 | Brown |
| 2011/0009793 A1 | 1/2011 | Lucero et al. |
| 2011/0046528 A1 | 2/2011 | Stevenson et al. |
| 2011/0082402 A1 | 4/2011 | Oddou et al. |
| 2011/0098618 A1 | 4/2011 | Fleming |
| 2011/0105971 A1 | 5/2011 | Ingimundarson et al. |
| 2011/0127390 A1 | 6/2011 | Brown |
| 2011/0137221 A1 | 6/2011 | Brown |
| 2011/0144551 A1 | 6/2011 | Johnson |
| 2011/0152737 A1 | 6/2011 | Burke et al. |
| 2011/0178448 A1 | 7/2011 | Einarsson |
| 2011/0184326 A1 | 7/2011 | Ingimundarson et al. |
| 2011/0266384 A1 | 11/2011 | Goodman et al. |
| 2011/0295169 A1* | 12/2011 | Hendricks ............... A61F 5/028 602/19 |
| 2012/0010547 A1 | 1/2012 | Hinds |
| 2012/0010749 A1 | 1/2012 | Van Der Merwe et al. |
| 2012/0022420 A1 | 1/2012 | Sandifer et al. |
| 2012/0029404 A1 | 2/2012 | Weaver, II et al. |
| 2012/0078151 A1 | 3/2012 | Cropper |
| 2012/0095373 A1* | 4/2012 | Hirata .................... A61H 3/00 601/35 |
| 2012/0172769 A1 | 7/2012 | Garrec |
| 2012/0179075 A1 | 7/2012 | Perry et al. |
| 2012/0184880 A1 | 7/2012 | Doyle |
| 2012/0197167 A1 | 8/2012 | Kruijsen et al. |
| 2012/0204381 A1 | 8/2012 | Ingimundarson et al. |
| 2012/0220910 A1 | 8/2012 | Gaylord et al. |
| 2012/0232450 A1 | 9/2012 | Garth et al. |
| 2012/0245502 A1 | 9/2012 | Garth et al. |
| 2012/0323154 A1 | 12/2012 | Ingimundarson et al. |
| 2013/0006158 A1 | 1/2013 | Ingimundarson et al. |
| 2013/0007946 A1 | 1/2013 | Brown |
| 2013/0012853 A1 | 1/2013 | Brown |
| 2013/0158457 A1 | 6/2013 | Garth et al. |
| 2013/0174326 A1 | 7/2013 | Takamoto et al. |
| 2013/0184625 A1* | 7/2013 | Ingimundarson ....... A61F 5/028 602/19 |
| 2013/0184628 A1 | 7/2013 | Ingimundarson et al. |
| 2013/0190670 A1 | 7/2013 | Von Zieglauer |
| 2013/0211302 A1 | 8/2013 | Brown |
| 2013/0237891 A1 | 9/2013 | Fryman et al. |
| 2013/0281901 A1 | 10/2013 | Ochoa |
| 2013/0298914 A1 | 11/2013 | Shibaya et al. |
| 2014/0033391 A1 | 2/2014 | Doyle |
| 2014/0081189 A1 | 3/2014 | Ingimundarson et al. |
| 2014/0100493 A1* | 4/2014 | Craig ..................... A61H 3/00 601/35 |
| 2014/0100501 A1 | 4/2014 | Burke et al. |
| 2014/0116452 A1 | 5/2014 | Ingimundarson et al. |
| 2014/0135672 A1 | 5/2014 | Joseph et al. |
| 2014/0158839 A1 | 6/2014 | Doyle |
| 2014/0207040 A1 | 6/2014 | Ingimundarson et al. |
| 2014/0200121 A1 | 7/2014 | Von Hoffmann et al. |
| 2014/0207041 A1 | 7/2014 | Ingimundarson et al. |
| 2014/0336020 A1 | 11/2014 | Von Hoffmann et al. |
| 2014/0371646 A1* | 12/2014 | Kozersky ................ A61F 5/028 602/19 |
| 2015/0048134 A1 | 2/2015 | Fawcett et al. |
| 2015/0076196 A1 | 3/2015 | Brown et al. |
| 2015/0217444 A1 | 8/2015 | Asada et al. |
| 2015/0316204 A1 | 11/2015 | Doyle |
| 2015/0366694 A1 | 12/2015 | Bujold et al. |
| 2016/0081871 A1 | 3/2016 | Doyle |
| 2016/0206497 A1 | 7/2016 | Deshpande et al. |
| 2016/0250061 A1* | 9/2016 | Ingimundarson ......... A61F 5/02 602/19 |
| 2016/0339583 A1 | 11/2016 | Van Engelhoven et al. |
| 2017/0007435 A1 | 1/2017 | Klutts |
| 2017/0156911 A1 | 6/2017 | Ingimundarson et al. |
| 2017/0173783 A1 | 6/2017 | Angold et al. |
| 2017/0189220 A1 | 7/2017 | Ingimundarson et al. |

FOREIGN PATENT DOCUMENTS

| | | |
|---|---|---|
| AU | 2010286851 A1 | 3/2012 |
| AU | 2010286851 A2 | 5/2012 |
| CA | 2112789 A1 | 8/1994 |
| CA | 2114387 A1 | 8/1994 |
| CA | 2767353 A1 | 1/2011 |
| CA | 2772296 A1 | 3/2011 |
| CH | 577282 A5 | 7/1976 |
| CH | 612076 A5 | 7/1979 |
| CH | 624001 A5 | 7/1981 |
| CN | 1311648 A | 9/2001 |
| CN | 1383799 A | 12/2002 |
| CN | 1461190 A | 12/2003 |
| CN | 101219079 A | 7/2008 |
| CN | 201101603 Y | 8/2008 |
| CN | 101444443 A | 6/2009 |
| CN | 101820783 A | 9/2010 |
| CN | 102470040 A | 5/2012 |
| DE | 1197192 B | 7/1965 |
| DE | 8804683 U1 | 6/1988 |
| DE | 3822113 A1 | 1/1990 |
| DE | 9417221 U1 | 1/1995 |
| DE | 9315776 U1 | 2/1995 |
| DE | 29503552 U1 | 4/1995 |
| DE | 19945045 A1 | 3/2001 |
| DE | 19940603 A1 | 4/2001 |
| DE | 20204747 U1 | 7/2002 |
| DE | 10329454 A1 | 1/2005 |
| DE | 202004015328 U1 | 2/2005 |
| DE | 202005007124 U1 | 6/2005 |
| DE | 102005017587 A1 | 4/2006 |
| DE | 202009004817 U1 | 9/2010 |
| EP | 0393380 B1 | 9/1992 |
| EP | 0589233 A1 | 3/1994 |
| EP | 0614624 A1 | 9/1994 |
| EP | 0614625 A1 | 9/1994 |

(56) References Cited

FOREIGN PATENT DOCUMENTS

| | | |
|---|---|---|
| EP | 0657149 A1 | 6/1995 |
| EP | 0589232 B1 | 11/1995 |
| EP | 0693260 B1 | 9/1998 |
| EP | 0651954 B1 | 2/1999 |
| EP | 1016351 A1 | 7/2000 |
| EP | 1159940 A2 | 12/2001 |
| EP | 1236412 A1 | 9/2002 |
| EP | 1342423 A1 | 9/2003 |
| EP | 1588678 A1 | 10/2005 |
| EP | 1743608 A2 | 1/2007 |
| EP | 1985264 A1 | 10/2008 |
| EP | 2200545 A1 | 6/2010 |
| EP | 2451412 A1 | 5/2012 |
| EP | 2473072 A1 | 7/2012 |
| FR | 1104562 A | 11/1955 |
| FR | 2757073 A1 | 6/1998 |
| FR | 2917323 A1 | 12/2008 |
| FR | 2952807 A1 | 5/2011 |
| GB | 826041 A | 12/1959 |
| GB | 909970 A | 11/1962 |
| GB | 2133289 A | 7/1984 |
| JP | H07246212 A | 9/1995 |
| JP | 3031760 U | 12/1996 |
| JP | H09273582 A | 10/1997 |
| JP | H10237708 A | 9/1998 |
| JP | 2000290331 A | 10/2000 |
| JP | 2001204851 A | 7/2001 |
| JP | 3091470 U | 1/2003 |
| JP | 2003175063 A | 6/2003 |
| JP | 2004016732 A | 1/2004 |
| JP | 2004041666 A | 2/2004 |
| JP | 2004160075 A | 6/2004 |
| JP | 2004209050 A | 7/2004 |
| JP | 2007291536 A | 11/2007 |
| JP | 3142546 U | 6/2008 |
| JP | 2008178618 A | 8/2008 |
| JP | 2008220883 A | 9/2008 |
| JP | 2009082697 A | 4/2009 |
| JP | 2012011550 A | 1/2012 |
| JP | 2013503268 A | 1/2013 |
| JP | 2013536010 A | 9/2013 |
| KR | 20150003562 U | 10/2015 |
| WO | 9401496 A1 | 1/1994 |
| WO | 9503720 A2 | 2/1995 |
| WO | 9532842 A2 | 12/1995 |
| WO | 9703581 A1 | 2/1997 |
| WO | 0053045 A1 | 9/2000 |
| WO | 2004110197 A2 | 12/2004 |
| WO | 2005086752 A3 | 4/2005 |
| WO | 2005086752 A2 | 9/2005 |
| WO | 2006121413 A1 | 11/2006 |
| WO | 2007003148 A1 | 1/2007 |
| WO | 2008031023 A2 | 3/2008 |
| WO | 2009017499 A1 | 2/2009 |
| WO | 2009017949 A1 | 2/2009 |
| WO | WO-2009017949 A1 * | 2/2009 ............ A61F 5/026 |
| WO | 2009052031 A1 | 4/2009 |
| WO | 2009068503 A1 | 6/2009 |
| WO | 2010141958 A1 | 12/2010 |
| WO | 2011005430 A1 | 1/2011 |
| WO | 2011025675 A1 | 3/2011 |
| WO | 2011066323 A1 | 6/2011 |
| WO | 2012029917 A1 | 3/2012 |
| WO | 2013016670 A1 | 1/2013 |
| WO | 2016138215 A1 | 9/2016 |
| WO | 2017109190 A1 | 6/2017 |

OTHER PUBLICATIONS

Etherington et al., "Hyundai's Future Mobility Plans Include Wearable Robotic Assistants," Tech Cruch, Dec. 19, 2016, 10 Pages, https://techcrunch.com/2016/12/19/hyundais-future-mobility-plans-include-wearable-robotic-assistants/.

"Ford Pilots New Exoskeleton Technology to Help Lessen Chance of Worker Fatigue, Injury," Ford Media Center, Nov. 9, 2017, 2 Pages, https://media.ford.com/content/fordmedia/fna/us/en/news/2017/11/09/ford-exoskeleton-technology-pilot.html.

"StrongArm Ergoskeleton Lift Assist Device V22," Strong Arm Technologies, Retrieved from the Internet on Apr. 14, 2018, 2 Pages, www.strongarmtech.com.

Pamphlet—"Bledsoe Phillippon K.A.F. Positioning Kit, Application Instructions (CP020205 Rev B 04/07), New Hip Arthroscopy Padding and Positioning Kit", Council Directive 93/42/EEC of Jun. 14, 1993 concerning Medical Devices, 2 pages.

Mehlman, Charles T. et al., "Hyphenated History: Knight-Taylor Spinal Orthosis"; American Journal of Orthopedics; Jun. 2000; pp. 479-483, vol. 29, Issue 6.

Pamphlet—"Bledsoe Phillippon K.A.F. Positioning Kit", Bledsoe Brace Systems, Medical Technology Inc., 2004, 2 pages.

Posture Control Brace. Soft Form, Orthopaedic by Design, FLA Orthopedics, Inc., 1 page; 2004. http://www.flaorthopedics.com.

Michael Pfiefer, MD et al., "Effects of a New Spinal Orthosis on Posture, Trunk Strength, and Quality of Life in Women with Postmenopausal Osteoporosis—a Randomized Trial", American Journal of Physical Medicine & Rehabilitation, vol. 83, No. 3, Mar. 2004, USA, pp. 177-186.

Scoliosis Specialists. About the SpineCor Brace; 2006-2012; http://www.scoliosisspecialists.com/aboutspinecorbrace.html. Retrieved from Internet on Aug. 1, 2013.

Hsu et al., "Principles and Components of Spinal Orthoses", AAOS Atlas of Orthoses and Assistive Devices, 4th Ed., Chapter 7, 2008, pp. 89-111.

Bledsoe Products, "Philippon K.A.F. Positioning Kit". Http://bledsoebrace.com/products/kaf.asp [retrieved from the internet May 10, 2012].

Spinomed Brochure—Spinal Orthosis for Vertebral Extension in Osteoporosis; Stellar Orthotics and Prosthetics Group, 2 pages, retrieved from Internet Sep. 23, 2013. http://www.stellaroandp.com/spotlight.html.

Sato, Ena et al., "Effect of the WISH-type hip brace on functional mobility in patients with osteoarthritis of the hip: evaluation using the timed UP & GO Test", Prosthetics and Orthotics International 2012 36:25 originally published online Nov. 17, 2011, http://poi.sagepub.com/content/36/125 [retrieved from internet on Jan. 22, 2014].

Silosheath Brochure, Soft Socket Gel Liner, 4 pages, 1994.

* cited by examiner

BODY INTERFACE

FIELD OF THE DISCLOSURE

A body interface, useable as an anterior-posterior orthosis, is provided for use as an exoskeleton having adjustability and means for proper placement over a hip and back of a user and is adapted to support an actuator or motion/energy storage module.

BACKGROUND

Exosuits or exoskeletons apply forces to the body in parallel with a user's muscles so walking or other repetitive motions results in less fatigue. These exoskeletons can give healthy individuals greater endurance or can provide small corrections to an impaired individual's gait.

An example of an exoskeleton is a multi-articular exoskeleton extending from the heel to the waist. The exoskeleton applies forces during transitions between legs, which is when the body uses the most energy. The calf muscles push the body upward and forward, while the thigh muscles swing the leg forward. The multi-articular exoskeleton can help or augment transitions or motions since it crosses both the ankle and hip joints.

Exoskeletons can aid a person performing physical labor and reduce the risk of injury from the lifting, bending, pulling, and pushing commonly required in many jobs. Assistive bionics technologies have the potential to improve quality of life, decrease at-work injury claims, and create a safer, more comfortable, and productive workplace environment.

Most exoskeletons comprise at least three components: a frame, an actuator or motion module (e.g. a motor, spring, etc.), and a physical body interface (often including straps, bindings, etc.). The exoskeletons may also include a power source supported by the frame for driving the actuator or motion module (should it be powered by an external source).

Good fit and ease and accuracy of adjustability are often challenges for the practical use of exoskeletons considering the length of use contemplated for many exoskeleton applications and the difficulty of conforming an exoskeleton, which includes rigid powered elements, to a user's dimensions in a comfortable manner. It is difficult to provide off-the-shelf or easy to manufacture exoskeletons that can adapt to the widely differing dimensions of different users, especially if the exoskeleton is worn successively by different users during different shifts.

In the instance of lumbar and hip supports, these supports for use as an exoskeleton are deficient in offering adjustability and proper placement over the hip and back of the user, and lack sufficient support and flexibility for comfortable and accurate placement over soft tissue while also permitting actuators to assist motion of the skeletal structure of the user. It may be difficult to properly place the support on a user because of the dynamic changes to a user's dimensions throughout use.

as a user may be susceptible to skin wounds and pressure sores of soft tissue adjacent the body interface at pressure points, particularly when used in combination of actuators driving the skeletal structure, a body interface should prevent any soft tissue irritation during use of the exoskeleton. Existing devices poorly address this issue, as the moving parts of the exoskeleton are often arranged to abut or rub against the user, particularly in the user's back.

The body interface also should be customized to an individual's own contours and anatomical needs, and the body interface should be adjustable to fit dimensions with different users. Existing devices fail to provide a comfortable interface between a body and an exoskeleton that can conform to a user's dynamically changing dimensions, contours, and other anatomical needs without sacrificing effective engagement with the exoskeleton.

From the foregoing, there is a need for a body interface suitable for an exoskeleton and configured for attachment to the user at multiple points to assist in supporting and coupling to the user's body, particularly in view of a user's dynamically changing dimensions and anatomical needs. There is further a need for a body interface that reduces forces on a user's lower back region while providing improved balance between adjustability and proper placement of the body interface.

SUMMARY

According to embodiments of the disclosure, the body interface is an improvement over known support interfaces in an exoskeleton, and reduces forces and torques on a user's lower back region. While described in a body interface, the embodiments disclosed and the individual components thereof, may likewise be extended to braces and supports in orthopedics, such as a spinal orthosis or an upper body orthosis.

The embodiments of the body interface include a lumbar support that serves as a suspension system to better accommodate and conform to the lumbar region of a user. Specifically, embodiments include lumbar tensioning to conform to a lumbar sacral shape, such as by increasing or decreasing purchase on demand, and to suspend a hip actuation device while forming a stable base for transmission of hip actuator forces (flexion and extension) through both a frame and a suspended soft good construction.

From these body interface embodiments, the body interface according to the disclosure provides increased breathability by using a lumbar support, such as an anatomically-shaped substrate formed from a non-stretch textile, that is suspended relative to a rigid frame or panel of the body interface. The lumbar support increases comfort by conforming to a user's anatomical shape. The lumbar support improves comfort and long-term use by reducing abrasion against a user by spacing the user's lumbar region a distance or clearance from the rigid frame or panel, by evenly distributing the forces to avoid pressure points, and by enhancing breathability and ease of donning and doffing.

The lumbar support securely sustains its place over soft-tissue while enabling actuators to drive the user's skeletal system, accommodating external movement relative or adjacent to the body interface without adjusting in placement against the user, enhancing the effectiveness of the exoskeleton. The lumbar support may be static because it maintains a fixed configuration, or may be dynamic in that a user can adjust tension of the lumbar support to adapt its conformability to the user and location relative to the frame. The body interface achieves an improved balance between proper support and comfortable fit for a user.

Embodiments of the body interface are adapted to anatomically improve donning and doffing of the body interface, and conformability to a user's waist and torso. A belt tensioning system enables the user to fasten the body interface to the user depending on intimacy of fit or lateral stabilization needed. The belt tensioning system includes three-dimensionally shaped belt arms that can readily open and close for ease and convenience of donning and doffing. The three-dimensionally shaped belt arms aid in singlehanded donning, which is useful for quickly and securely securing the body interface to a user.

The belt tensioning system preferably has a soft-good construction including textile, foam, and semi-rigid plastic backing to yield an "anatomically shaped resting position," that can be modified when donning the body interface and securely placing about the user. This allows for a natural and comfortable positioning of the body interface.

The body interface has versatility for supporting hip musculature and comfortably remaining in place as actuators assist a user with hip flexion and extension. The body interface is versatile further in supporting an anterior panel that can be added for additional truncal support for moderate hip/truncal extension assistance. The body interface can additionally support a posterior panel extension and shoulder straps to provide enhanced support and assistance for users with truncal weakness or during sit-to-stand activities. In this way, the body interface may be constructed and adapted modularly for easy and convenient adaptation to a user's specific and dynamic needs.

The above embodiments solve the problem of existing exoskeletons and body interfaces having improper balance between comfort and effectiveness by providing an improved lumbar support suspension system with a tensioning system and combines breathability, comfort, and enhanced conformity, improved belt arms for easier donning and offing, and improved versatility toward assistance for users with truncal weakness or for different activities.

The drawings and figures are not drawn to scale, but instead are drawn to provide a better understanding of the components, and are not intended to be limiting in scope, but to provide exemplary illustrations. The figures illustrate exemplary configurations of a body interface, and in no way limit the structures or configurations of a body interface and components according to the present disclosure.

DETAILED DESCRIPTION OF VARIOUS EMBODIMENTS

The embodiments of the disclosure relate to a body interface.

The body interface incorporates features in a spinal orthosis, such as a spinal orthosis disclosed in U.S. patent application publication 2017/0007435, published on Jan. 12, 2017. However, unlike in a spinal orthosis which is specifically designed for pain relief, protecting injured ligaments or muscles, and post-surgical immobilization, the body interface of the embodiments of the disclosure are provided for support over soft tissue while permitting mechanical actuators to assist motion of skeletal structures. The body interface, like the known spinal orthosis, may be configured to relieve pressure over the spinous processes while applying an even pressure to the paraspinal musculature to ensure comfortable support of the exoskeleton equipment.

A known spinal orthosis, such as the exemplary spinal orthosis described in U.S. Pat. No. 8,172,779, granted on May 8, 2012 and incorporated by reference, and the embodiments of the body interface, have outer and inner side configurations, with the inner side arranged to be adjacent the user's back. The orthosis and body support have first and second belt members, and a compression or closure system adapted to exert pressure onto the lumbar region of a user's back. The compression or closure system includes tightening elements or drawstrings that permit the user to adjust pressure over the back and a cover extending over the compression system.

While in the spinal orthosis there is a flexible or semi-rigid back plate extending over at least part of the compression system, the body interface preferably has a rigid or semi-rigid frame that may include a posterior panel arranged to be adjacent the back of the user and to carry actuators and/or a power supply. An anterior panel may be attached to the body interface on an anterior side thereof.

Figure 1A:
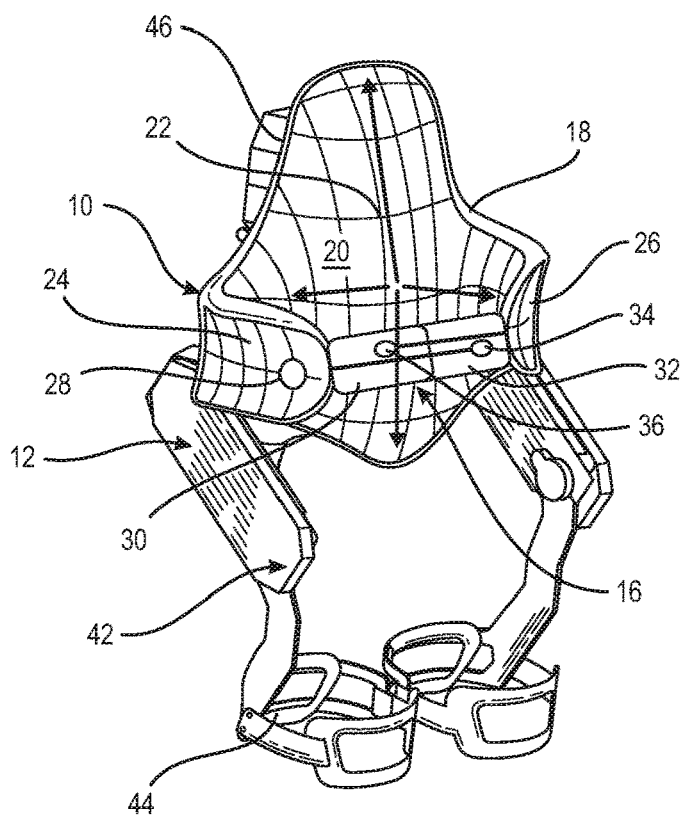
FIG. 1A is a schematic view of an exoskeleton including a body interface according to embodiments of the disclosure.

Referring to FIG. 1A, a body interface 10 includes a frame, as in a panel 18 that is semi-rigid or rigid, and a lumbar support 22 anchored to the panel 18 at an anchor point. The lumbar support 22 may be tensionable over and spaced a distance apart from the panel 18. The lumbar support 22 preferably has a segment spaced apart from the panel 18 to match and increase lumbar support 22 to a shape and weight of a user over a sacral area, while being suspended from the panel 18. The body interface 10 is stabilized on a user's muscle and soft-tissue, while remaining stable in position on the user according to relative movement of an assistive system 12 attachable to the body interface 10 providing stability without sacrificing comfort or adaptability.

The lumbar support 22 may flexible relative to the panel 18; however, the lumbar support 22 is preferably a non-stretchable textile or other suitable material. In a variation, the lumbar support 22 may be stretchable or have stretchable components or segments. The lumbar support 22 may be static because it is not adjustable in tension aside from bearing weight from a user, or it may be dynamically adjustable because the lumbar support 22 is tensionable relative to the panel by one or more tensioning devices 28, 29.

Figure 1B:
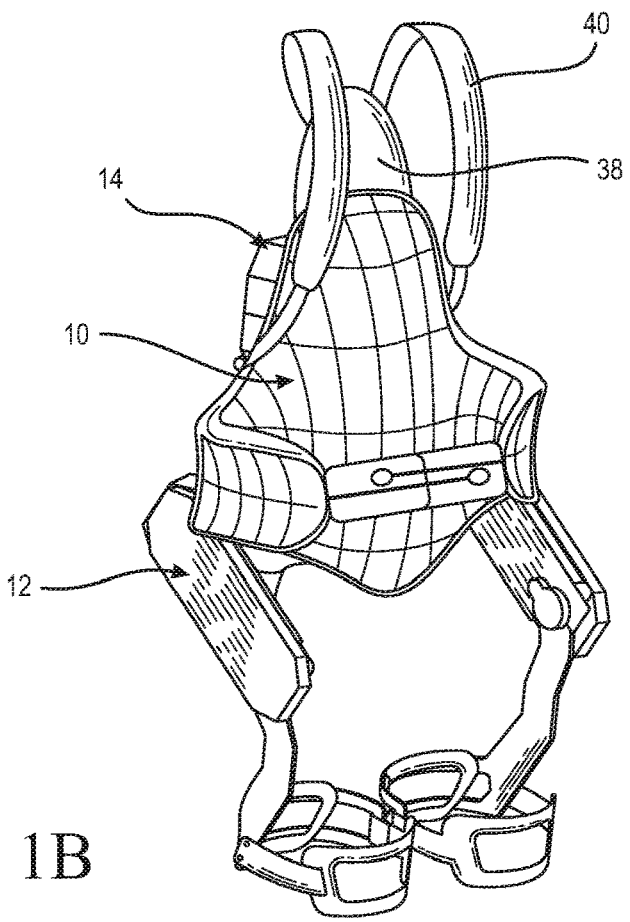
FIG. 1B is a schematic view of the exoskeleton of FIG. 1A including a posterior panel extension.

The body interface 10 is preferably connected to an assistive system 12 movable relative to the panel 18, and a power supply 14 adapted to drive the assistive system 12. In FIGS. 1A and 1B, the assistive system 12 includes a leg/hip assist mechanism 42 and a leg connection 44, preferably on lateral sides of the panel 18. The driving system or power supply 14 includes a driving mechanism 46 for driving the leg/hip mechanism 42, and is preferably on a posterior side of the panel 18.

The panel 18 is arranged to control sagittal movement, thereby reducing gross and intersegmental flexion and extension of the hip(s) and trunk. The panel 18 is arranged to control coronal movement (with the arms) to control spinal/hip motion of lateral bending and abduction, respectively. The panel 18 may likewise be arranged to control flexion-extension movement.

As shown in FIG. 1B, the body interface 10 may include a panel attachment 38 for attaching to the panel 18 superiorly, the panel attachment 38 including a strap system 40.

Figure 3:
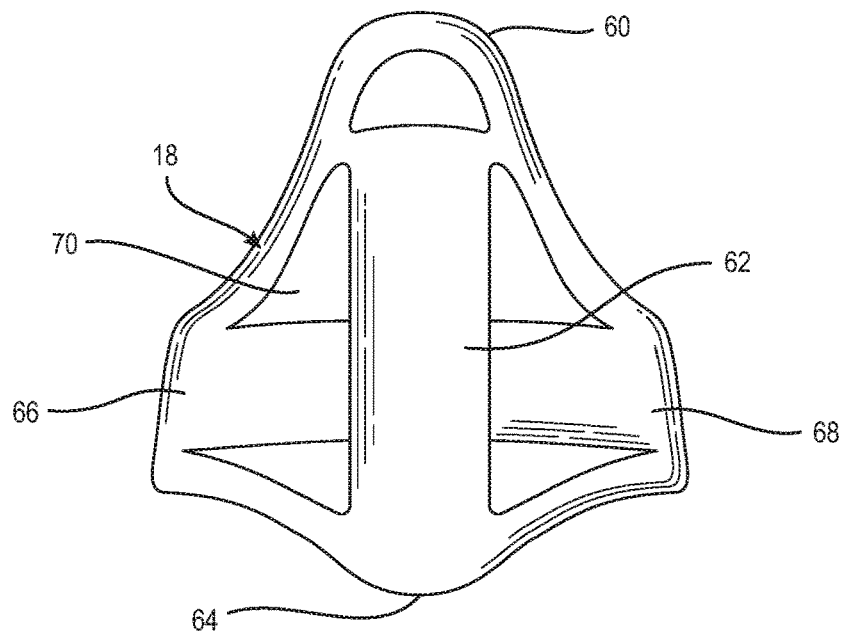
FIG. 3 is a perspective view of a frame in the body interface of FIG. 1A.

Referring to FIG. 3, the panel 18 may be arranged with a superior or thoracic portion 60, an inferior or sacral portion 64, and a central or lumbar portion 62 between the superior portion 60 and the inferior portion 64. The panel 18 may define first and second lateral portions 66, 68 extending from the central portion 62. The panel 18 may define a plurality of openings 70.

Figure 2:
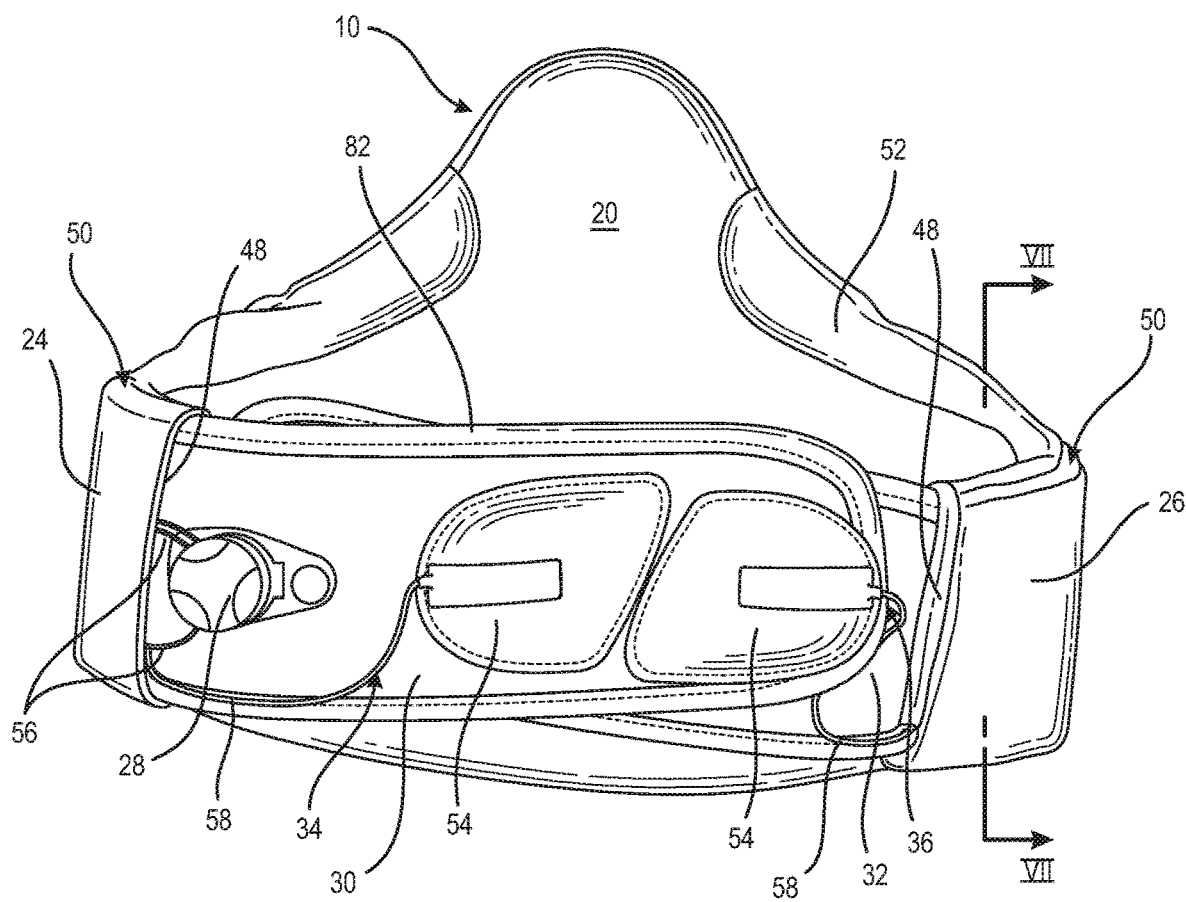
FIG. 2 is a perspective view of an embodiment of the body interface of FIG. 1A.

As shown in FIGS. 1A-2, the body interface 10 includes an attachment system 16 secured to the panel and creating a circumference with the panel 18. The attachment system 16 may share a pulley system described in U.S. patent application publication no. 2017/0007435, and U.S. Pat. No. 8,172,779. A cover 20 extends over the lumbar support 22 between the cover 20 and the panel 18, or the lumbar support 22 is part of the cover, as disclosed below in other embodiments.

FIG. 2 shows the body interface 10 including first and second arms 24, 26 on opposed lateral sides of the panel 18 through which first and second belt segments 30, 32 of the attachment system 16, respectively, extend to engage one another. At least one tensioning element 34, 36 is movable relative to the panel 18 to tension the attachment system 16 by reducing the circumference thereof. The at least one tensioning element 34, 36 secures to one of the first and second belt segments 30, 32 of the attachment system 16 and is adapted to move the first and second belt segments 30, 32 relative to the panel 18. The first and second arms 24, 26 are preferably curved so that the first and second arms generally hug or closely embrace the body of the user. Such a configuration aids the donning and assures that the body interface remains securely on the user, particularly in view of the weight and movement of the activation system.

The body interface 10 has first and second arms 24, 26 which extend from opposed lateral sides of the panel 18, the first and second arms 24, 26 forming open channels 48 through which the first and second belt segments 30, 32 slidably extend. The first and second arms 24, 26 pivot relative to the panel 18 according to tensioning of the attachment system 16 to form a curvature 50. The first and second arms 24, 26 have upper portions 52 permitting flexure of the first and second arms 24, 26 to enable formation of the curvature 50.

According to an exemplary embodiment, the tensioning device 28 for regulating tension in the lumbar support 22 includes a cable 56 extending through the channel 48 to engage the lumbar support 22 and a dial tensioning device. The tensioning mechanism may be a dial tensioning device, a ladder strap or other suitable incremental tensioning mechanism, as taught in U.S. Pat. No. 7,198,610, issued on Apr. 3, 2007.

The tensioning element 34 includes an elongate element 58 and a handle 54 secured to an end of the elongate element 56. The handle 54 is securable over a belt segment 30 and the elongate element 58 is movable relative to the belt segment 30. The first and second belt segments 30, 32 are securable to one another by cooperating fasteners 82. The tensioning element 34 may be arranged similarly as in U.S. patent application no. publication 2017/0007435.

Figure 4A:
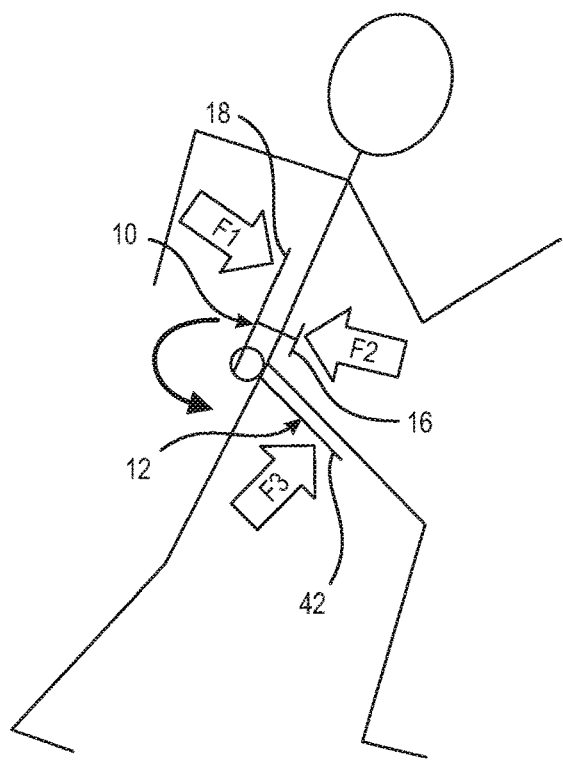
FIGS. 4A and 4B are force diagrams showing forces in flexion of the exoskeleton of FIG. 1A on a user wearing the body interface.
Figure 4B:
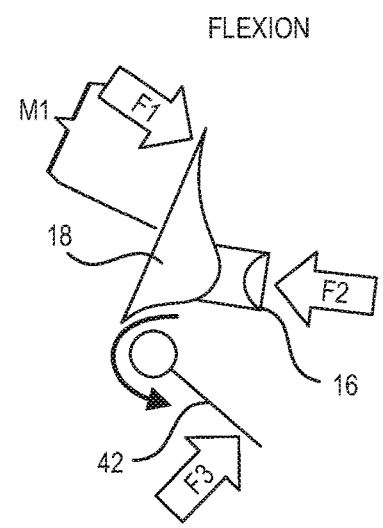

FIGS. 4A and 4B show hip flexion actuation schema:
(A) Actuator 42 drives thigh cuff/hip into flexion with force F3. The force F3 requirements may be smaller relative to other forces depicted in FIGS. 4A and 4B in that they may be generated to advance the non-weight bearing leg during swing phase.
(B) Attachment system 16 is the middle counter force F2.
(C) Counterforce F1, acting counter to a hip flexion moment generated by the actuator, is provided at a superior portion of panel 18. M1 represents a moment arm of the counterforce or stabilizing force F1. The length of the moment arm M1 is relatively long, and sufficient leverage counters the force/moment generated by the hip actuator 42.

Figure 4C:
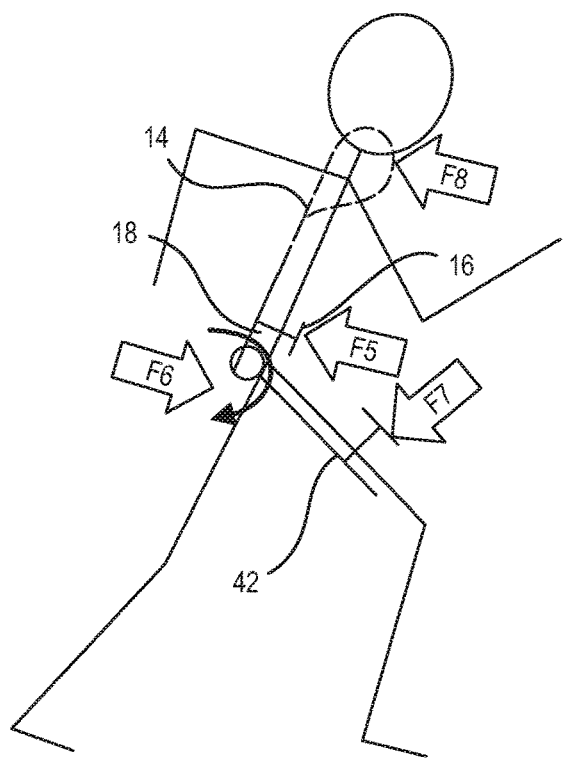
FIGS. 4C and 4D are force diagrams showing forces in extension of the exoskeleton of FIG. 1A on a user wearing the body interface.
Figure 4D:
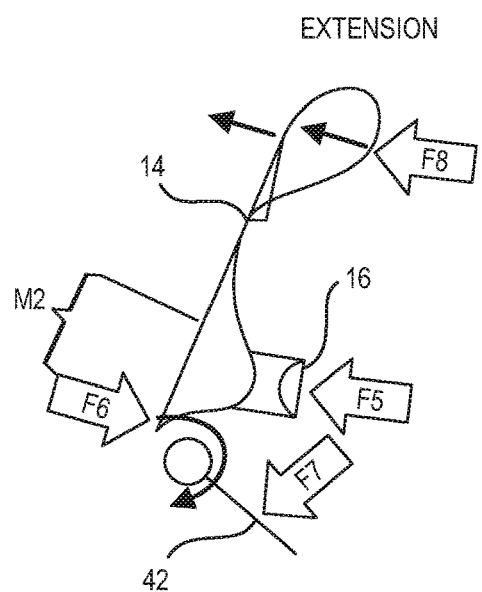

FIGS. 4C and 4D show hip extension activation schema:
(A) Actuator drives thigh cuff/hip into extension with force F7;
(B) Middle counterforce F5 is provided from waist to distal posterior panel edge F6, yet this counterforce is relatively small. The moment arm M2, which is countering the actuator's extension force/moment is short (shorter than M1), and additional stabilization superiorly is needed, which is comprised in a panel extension and shoulder straps. It could also be provided by strap; and
(C) requires assistance of panel extension and shoulder loops. Force F8 can help to pull the shoulders and trunk into extension during a sit-to-stand maneuver.

In the event of a weak trunk, there is a need to create extension up the back by making a longer moment arm, particularly when a user is aiming to stand up. The force required to generate advancement of the thigh is low since it involves only the weight of the leg. The moment arm of the leg is diminished by the flexing of the knee. With hip flexion actuation overall stabilization, the forces required by the interface are low. For hip flexion force, the requirement is much lower as simply picking up the leg is required. The moment arm only goes to the knee joint whereby the lower leg flexes below the knee. If the user already has sufficient strength in trunk stability, they may be able to effectively balance the trunk over the actuators. If on the other hand trunk weakness exists, the interface may be required to provide adequate stabilization over the actuators.

The stabilizing forces required to offset the actuator's generation of adequate torque to provide sit-to-stand assistance, however, are high since it must move/stabilize most of a user's body weight against gravity during a weight bearing activity. This demonstrates the likely need for the additional stabilization, such that adding the anterior panel to the belt or even the posterior panel extension and shoulder straps for sit-to-stand motions or truncal weakness. The body interface is configured to be constructed modularly, such that the posterior panel extension and shoulder straps and/or anterior panel may be added or removed at any point during treatment or use, based on the user's current needs.

Figure 5:
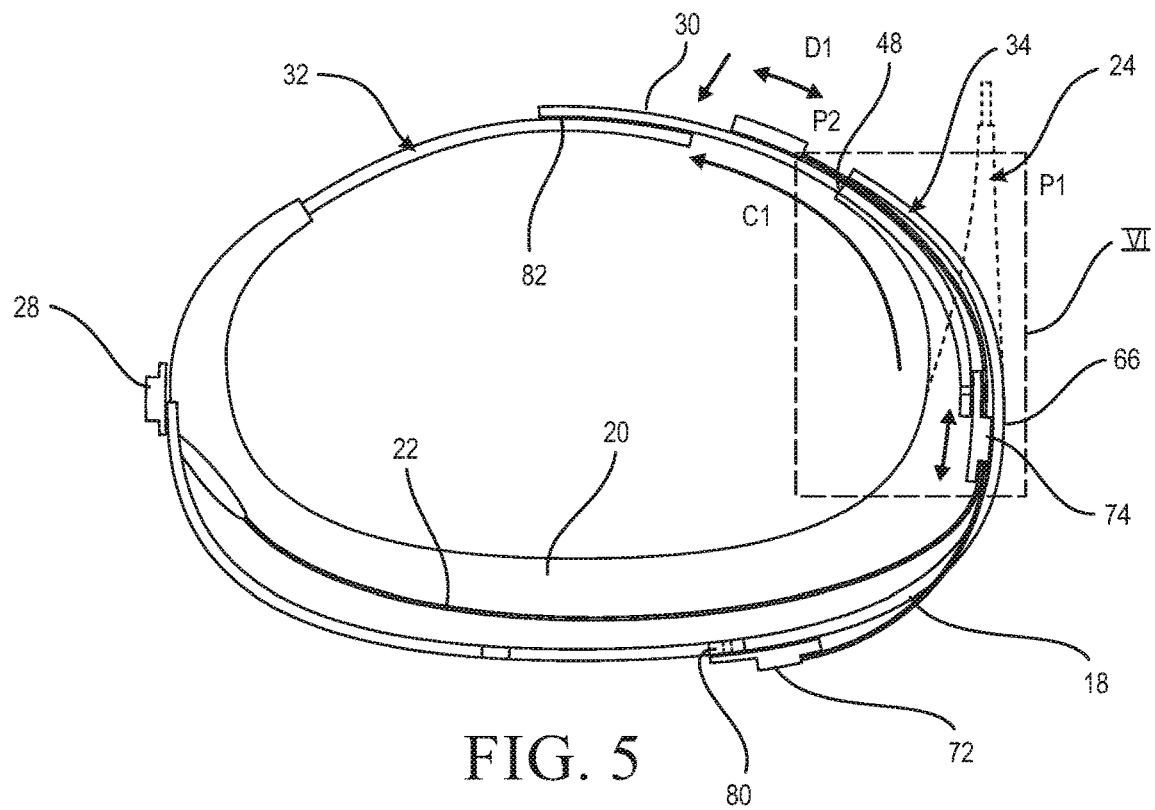
FIG. 5 is a schematic plan view of the body interface of FIG. 2.
Figure 6:
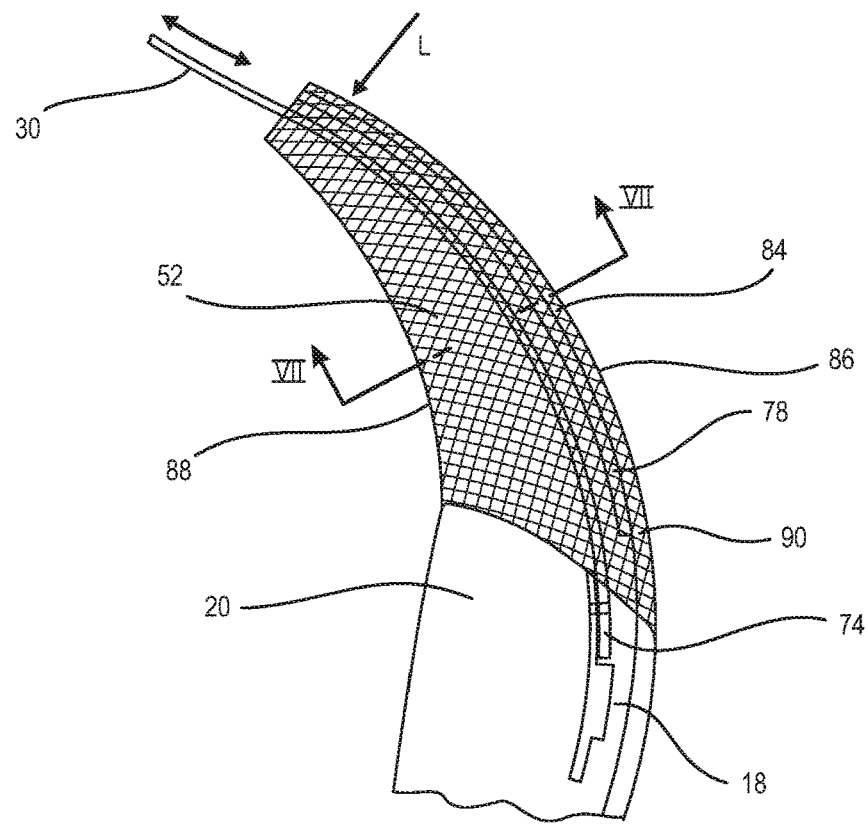
FIG. 6 is a schematic detail view VI of FIG. 5.
Figure 7:
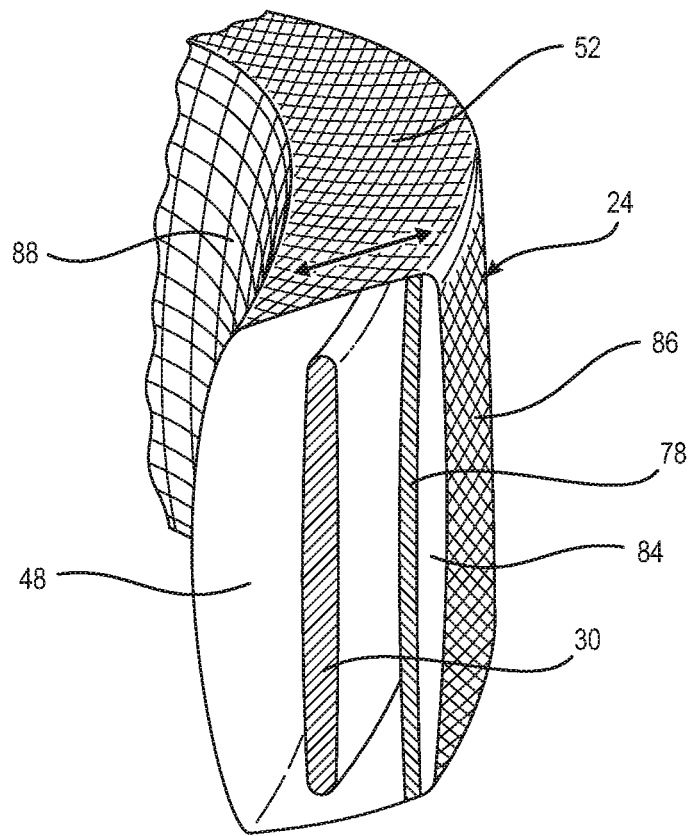
FIG. 7 is a cross-sectional view taken along line VII-VII in FIG. 6.

As shown in FIG. 5, the body interface 10 comprises a routing unit 72 secured to the panel 18 and connecting to a routing carriage 74 by a first segment tensioning element 76, the routing carriage 74 slidable along a lateral side 66 of the panel 18, a second tensioning element 34 extending from the routing carriage 74 through the first arm 24. The routing unit 72 is fixedly secured to the panel 18 at an anchor 80.

The first arm 24 includes a plate 78 extending from an end of the lateral portion 66 of the panel 18 and lining the open channel 48 within the first arm 24. The plate 78 resists yet yields to movement of the first belt segment 30 as it is drawn toward the second belt segment 32 to define an inner curvature C1. The first arm 34 generally has a straight profile (S) if symmetrically constructed in a configuration P1, however the first arm 34 has a curved profile C1 in an asymmetrical configuration P2 where the inner textile 88 is shorter in circumference than the outer textile 86, the connection made through the elastic textile forming the top layer 52 creates the 3D anatomical shape at rest. Once the body interface 10 is donned, the shape is not caused by tensioning but through connection of differing dimensions of internal/external materials 88, 86, 52, allowing the body interface 10 to conform simply and automatically to the user's dynamic dimensions.

The first arm 34 defines inner and outer surface layers comprising the inner and outer textiles 86, 88 and a top layer 52 spanning between the inner and outer surface layers 86, 88, such that the top layer 52 is more elastic than the inner and outer surface layers 86, 88. The inner and outer surface layers 86, 88 are substantially inelastic and the top layer 52 is comparatively elastic. The inner layer 86 defines an extension of the cover 20 extending about the panel 18.

The different elasticities of the materials of layers 52, 86, 88 allows the body interface 10 to assume a shape when donned by the user that conforms to the user's dimensions, thereby distributing pressures and contact evenly on the user's skin. This reduces or altogether eliminates pressure points and other discomforts experienced in existing exoskeleton interfaces.

A plate 78 lines a channel 48 within arm 24, and may be flexible and semi-rigid. The plate 78 is preferably formed from plastic. The plate 78 has a generally predetermined straight profile and resists but ultimately is bendable to a curved profile due to exertion of a load L bringing the first arm 24 into the curved profile C1. The plate 78 generally returns to the straight profile S upon release of the load L.

The resting shape of the textile construction is due to constraining the materials through connections and dimensions. The load L is created not by an external force or even the circumferential compression by the tensioned belt arms, but rather by the pulling toward the center by the constrained shorter non-stretch textile forming the inner layer 88. This results in a simple and automatic mechanism to allow the cover 20 and the panel 18 to cooperate for optimal effectiveness and comfort.

A padding layer 84 extends along the plate 78 and between the plate 78 and the outer layer 86. A lateral portion end 90 of the panel 18 preferably overlaps the plate 78. The belt segment 30 is adapted to slide within the channel 48, while the first arm 24 maintains its shape without interfering with the sliding of the belt segment 30. The features described regarding first arm 24 apply correspondingly to second arm 26 and to belt segment 32.

Figure 8:
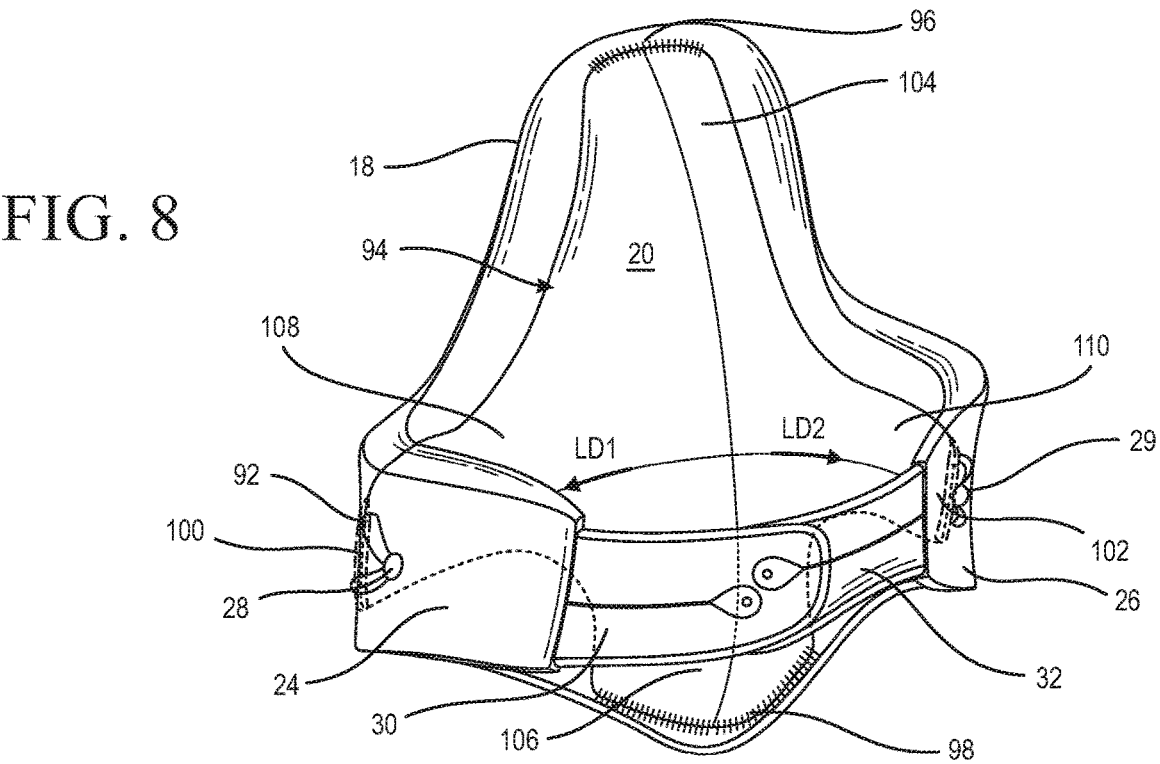
FIG. 8 is a perspective view of another embodiment of the body interface having a variation of the lumbar support.

Referring to the embodiment of a body interface depicted in FIG. 8, a tensioning element 92 connects to the lumbar support 94 and is movable in a generally lateral direction LD1, LD2 relative to the panel 18. The tensioning device 28 is arranged to permit regulation of the tensioning element 92 to move an end 100, 102 of the lumbar support 94 relative to the panel 18.

The lumbar support 94 has first, second lateral portions 108, 110 coupled to first, and second tensioning devices 28, 29 each arranged to draw the first and second lateral portions 108, 110 in opposed directions LD1, LD2 relative to one another via the tensioning element 92 which extends between the first and second tensioning devices. The lumbar support 94 is anchored superiorly on the panel 18 at a superior attachment 96, and is anchored inferiorly on the panel 18 at an inferior attachment 98. The first and second lateral portions 108, 110 are defined such that the first and second lateral portions 108, 110 are movable relative to the superior and inferior portions 104, 106, according to regulation by the first and second tensioning devices 28, 29.

According to an embodiment, the lumbar support 94 is formed from a continuous sheet of unstretchable material. In another embodiment, the lumbar support 94 is a multi-sheet construction, wherein the superior, inferior and first and second lateral portions 104, 106, 108, and 110 may have different stretchability relative to one another.

The superior and inferior fixations or attachments 96, 98 secure the cover 20 and the lumbar support 94 along the panel 18 while ensuring that the lumbar support and the first and second lateral portions 108, 110 may change configuration to conform to the user's dynamic dimensions, such as during movement of an exoskeleton attached to the body interface. For example, the cover 20 and the lumbar support 94 may abut a user's body as the panel 18, spaced in some embodiments a distance apart from the lumbar support 94 due to the tensioning of lumbar support 94, cooperates with the exoskeleton. This arrangement reduces or eliminates pressure points, thereby enhancing comfort, without sacrificing effective engagement with the exoskeleton.

Similarly, the arrangement of the lateral portions 108, 110 and the arms 24, 26 in relation to the panel 18 allows for the arms 24, 26 to comfortable engage a circumference of a user while shifting in configuration relative to the panel 18, due to the properties of the lumbar support 94 and the materials forming the lumbar support 94.

Figure 9:
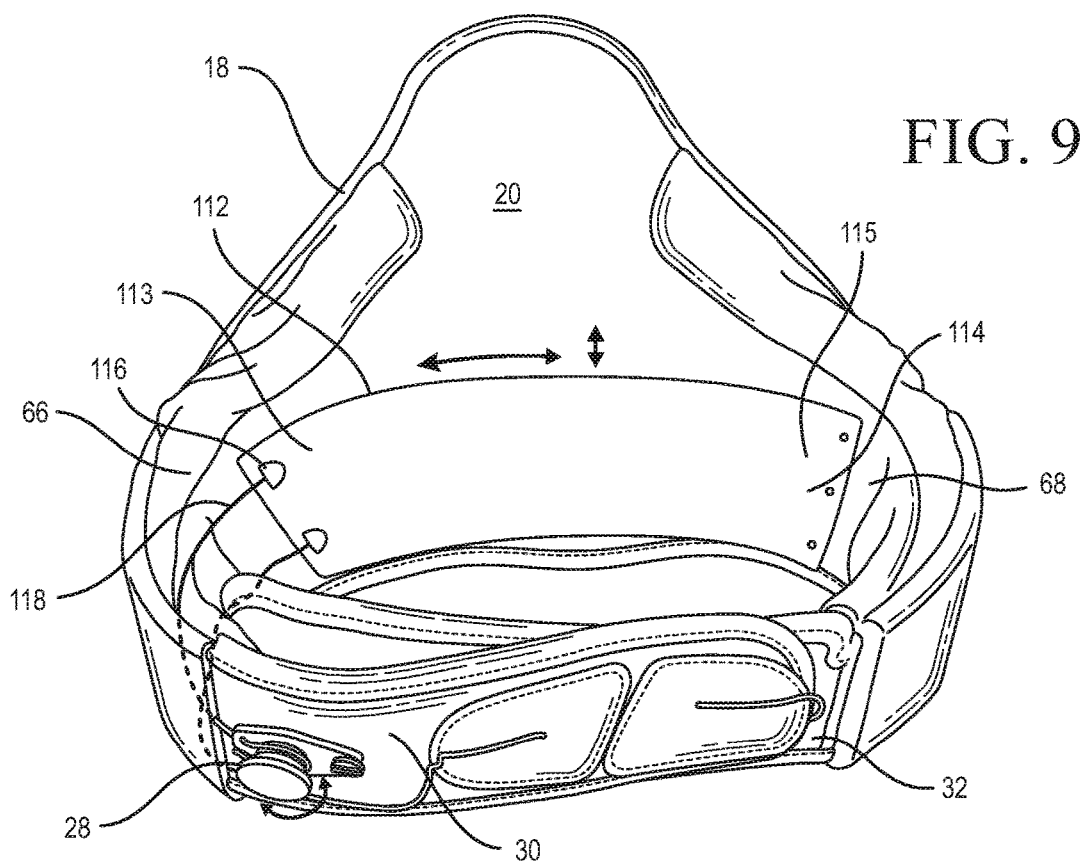
FIG. 9 is a perspective view of another embodiment of the body interface having a variation of the lumbar support.

In another embodiment of the lumbar support 112 in FIG. 9, the lumbar support 112 has a first lateral side 113 coupled to a tensioning device 28, and a second lateral side 115 anchored to a second lateral side 68 of the panel 18. The tensioning device 28 is arranged to pull the first lateral side 113 from the second lateral side 115. The tensioning device 28 has a tensioning element 118 coupled at a connector 116 attached to the first lateral side 113 of the lumbar support 112.

The lumbar support 112 preferably defines a band 114 extending between the first and second lateral sides 66, 68 of the panel 18. The lumbar support 112 is preferably only secured to the panel 18 at the second lateral side 68. This arrangement advantageously provides for simple and symmetrical control of the tensioning over the entire lumbar support 112 via the single tensioning device 28.

Band 114 additionally provides stability and control between the tensioning of first and second lateral sides. In certain embodiments, the band 114 may be more rigid or inflexible than the cover 20 or lumbar support 112, thereby supporting and evenly distributing pressure over a desired region or surface of the user's lumbar or sacral area. In certain embodiments, the band 114 may be arranged to provide, in addition to tensioning, optimal support and pressure distribution along key portions of the user's lumbar or sacral regions. A skilled artisan will understand that the band 114 may be of different configurations and in different locations than the depicted embodiment of FIG. 9.

Figure 10:
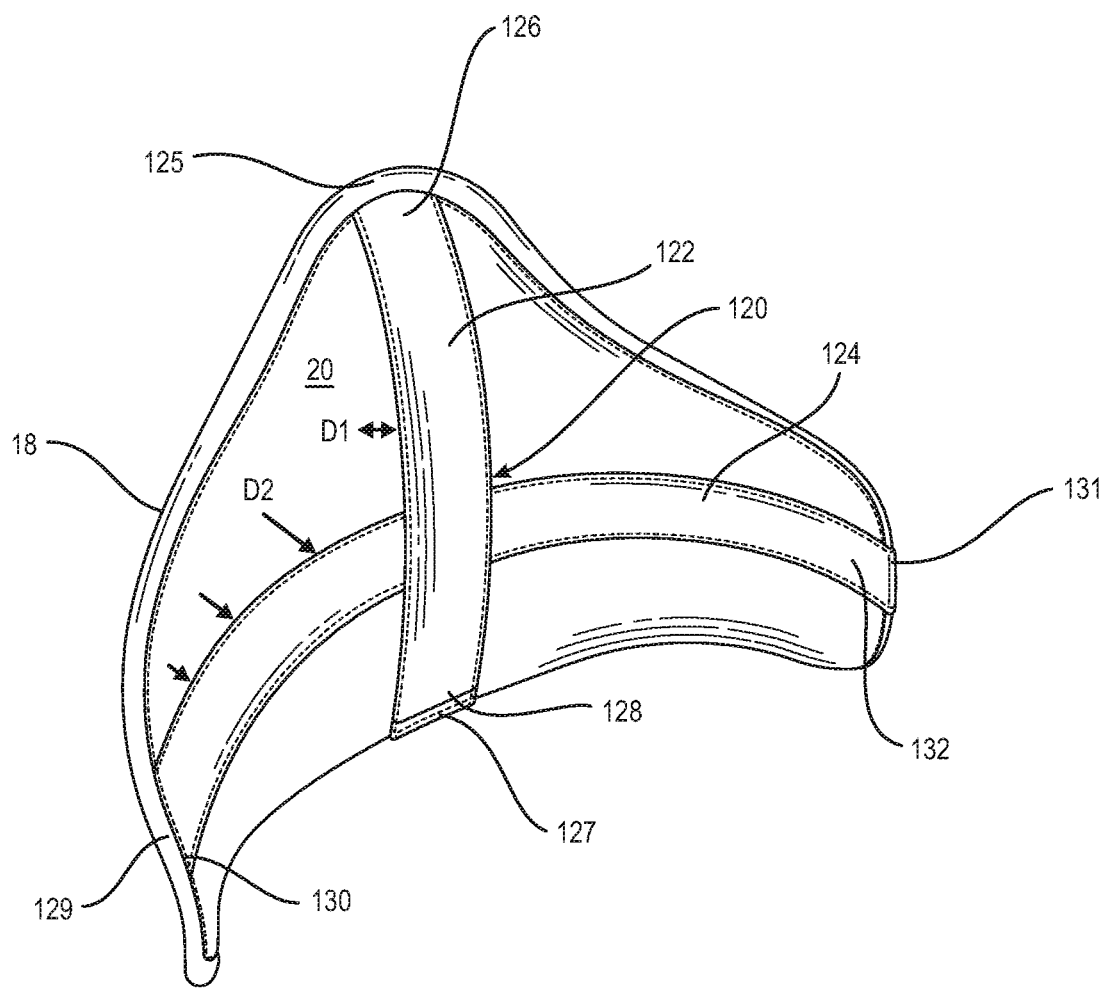
FIG. 10 is a perspective view of another embodiment of the body interface having a variation of the lumbar support.

In yet another embodiment of the lumbar support in FIG. 10, the lumbar support 120 comprises a first band 122 having superior and inferior portions 126, 128 secured to superior and inferior ends 125, 127 of the panel 18. The first band 122 is tensioned between the superior and inferior ends 125, 127 to be spaced apart by a clearance from the panel 18 between such superior and inferior ends 125, 127, the clearance being greatest at a center portion of the first band 122 between the superior and inferior portions 126, 128.

The lumbar support 120 comprises a second band 124 having first and second portions 130, 132 secured to first and second lateral ends 129, 131 of the panel 18. The second band 124 is preferably spaced apart a clearance D2 from the panel 18 between such first and second lateral ends 129, 130. The clearance D2 may be greatest at a center portion of the second band 124 between the first and second lateral ends 130, 132. First and second bands 122, 124 may be configured to resemble and coextend with the standard curvature of a user's sacral or lumbar region, thereby providing optimal engagement between the user and the lumbar support 120.

First and second bands 122, 124 provide close engagement between the lumbar support 120 and a user, thus providing enhanced comfort even through a user's dynamic motions when using an exoskeleton engaged with the body interface 10. By providing distances D1, D2 between the user and the lumbar support 120, a comfortable and even distribution of pressure is achieved without compromising the engagement of the body interface, exoskeleton, and the user. This reduces or altogether eliminates the problem of pressure points resulting from exoskeleton components abutting or rubbing against the user's body.

Figure 11A:
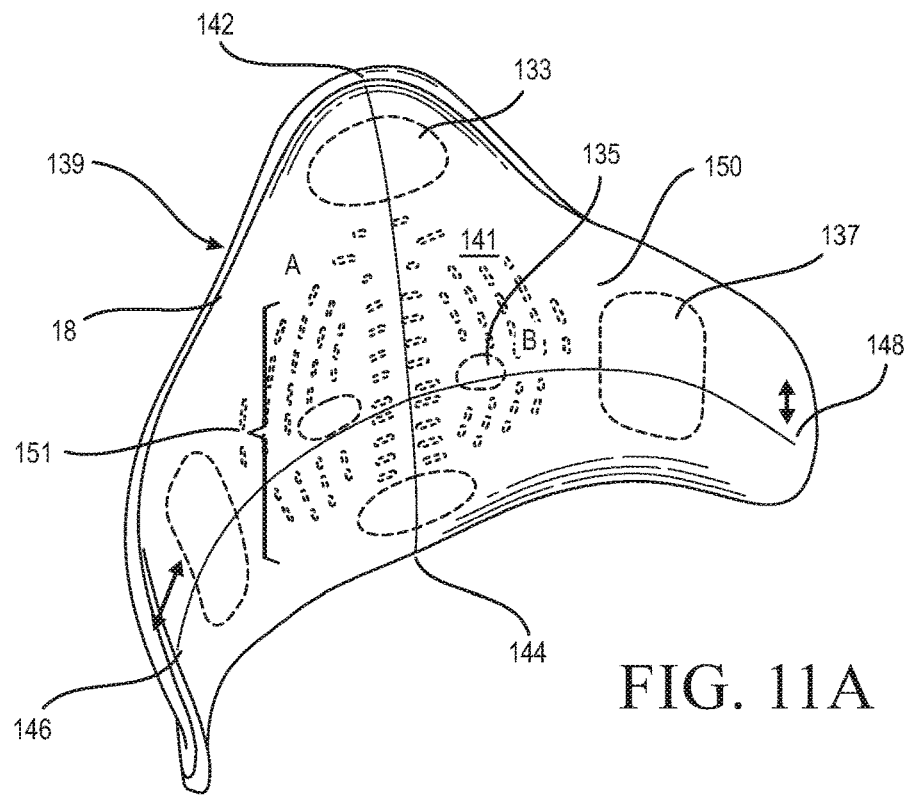
FIG. 11A is a perspective view of another embodiment of the body interface having a variation of the lumbar support having a first tension configuration.
Figure 11B:
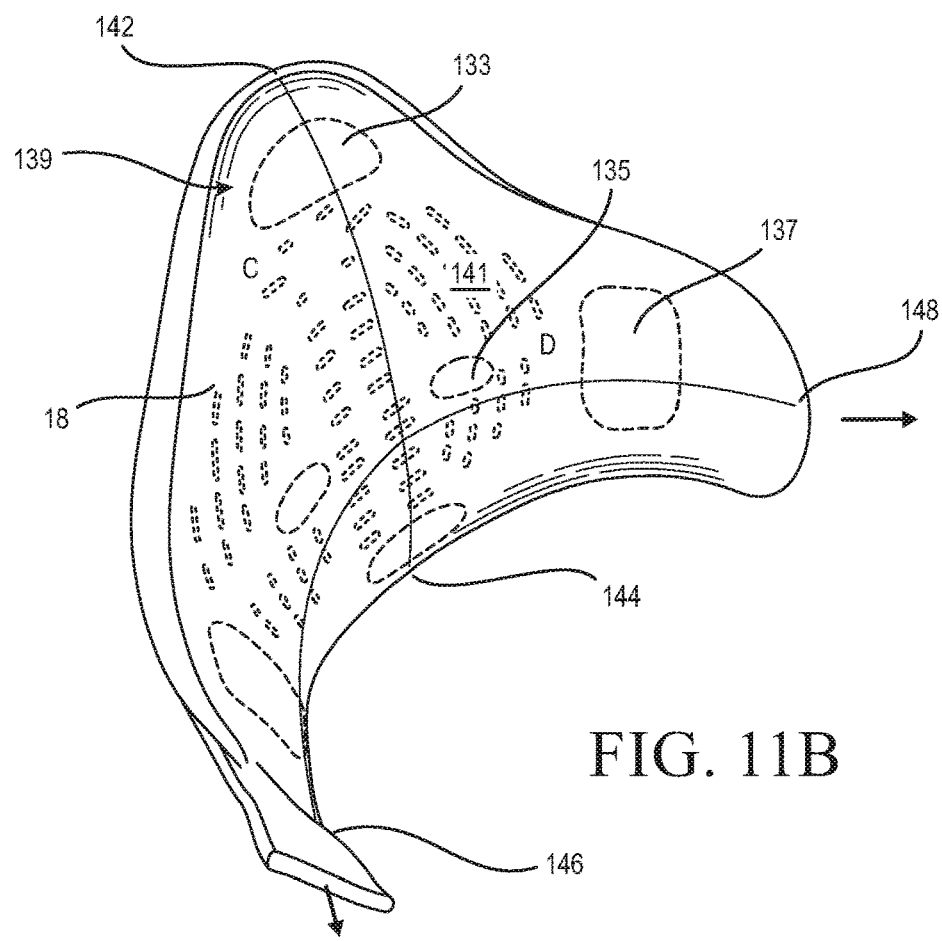
FIG. 11B is a perspective view of the body interface of FIG. 11A having a second tension configuration.

In FIGS. 11A and 11B, the cover 141 over the panel 18 serves as the lumbar support 139. The cover 141 is preferably a non-stretch textile that is tensioned and secured at superior and inferior ends 142, 144, and likewise tensioned at the first and second lateral ends 146, 148. The superior and inferior ends 142, 144 are constrained to the panel or frame 18, and form Arc A therebetween. The lateral ends 146, 148 are permitting to be yet further tensioned, and form Arc B therebetween. Both Arcs A and B are spaced apart from the panel 18, and suspended over the panel 18. The cover 141 may be formed of a textile that allows for defining a perforated texture that provides enhanced breathability and light-weight construction to provide optimal comfort for a user. FIGS. 11A and 11B illustrate a lumbar curve reshaping method to improve purchase on the back for adequate suspension of the actuators and to conform better for comfort. The arc B between the lateral ends 146, 148 can be shortened, creating more tension between the lateral ends 146, 148, and the superior and inferior ends 142, 144, which creates a new configuration of the lumbar support 139. The panel 18 is pulled inward at lateral ends 146, 148, which creates a new arc D. The reduced circumferential dimension along Arc D also reshapes Arc A into the new Arc C.

A plurality of apertures 150 may be defined by the panel 18, and arranged in a circular pattern 152 of apertures 150. Including apertures 150 in a specific pattern 152 advantageously imparts desired breathability, flexibility, and attachment points on the panel 18. In the depicted embodiment, providing apertures 150 in arcs 152 may allow the panel 18 to yield to circumferential bending to a desired degree as the cover 141 is tensioned to better encircle and contact a user's waist. A skilled person will recognize that the features of the depicted embodiment are illustrative only, and that additional patterns of apertures allowing for desired movement, bending, or other advantages may be provided in other embodiments.

The embodiment depicted in FIGS. 11A and 11B provides a simple and intuitive mechanism for conforming the panel 18 and the cover 141 to the dimensions of a user. Using cover 141 as a lumbar support is advantageous because it provides for enhanced breathability, simplicity, and reduction of material costs, while still allowing for a dynamic engagement between the body interface 10, the user, and an exoskeleton.

The lumbar support/cover 141 may be shaped based on the properties of the materials forming the cover 141, or may receive its shape based on tension applied to the panel 18 by the user via tensioning devices that may be used under other embodiments in the present disclosure.

By providing a cover 141 that attaches to panel 18 at key locations, such as near the extreme edges of the panel 18, the device can cooperate with and transmit forces generated through user motions, such as through exoskeleton-assisted motions, while providing even pressure distribution, comfort, and enhanced dynamic conformity with the user.

Figure 12A:
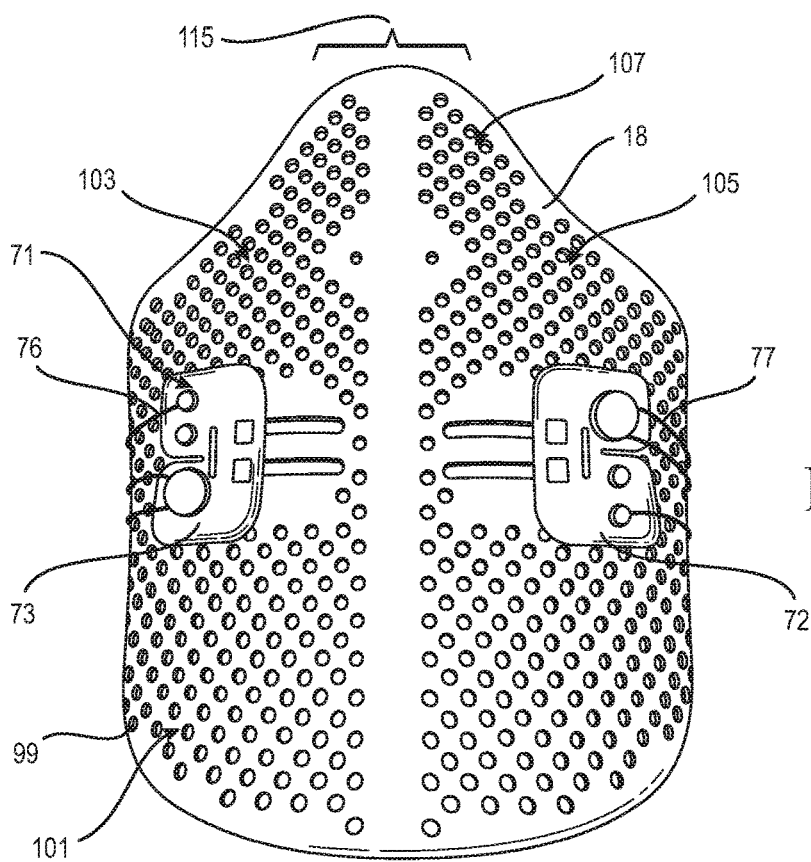
FIG. 12A is a schematic posterior view of the body interface of FIG. 2 having a belt tensioning system.
Figure 12B:
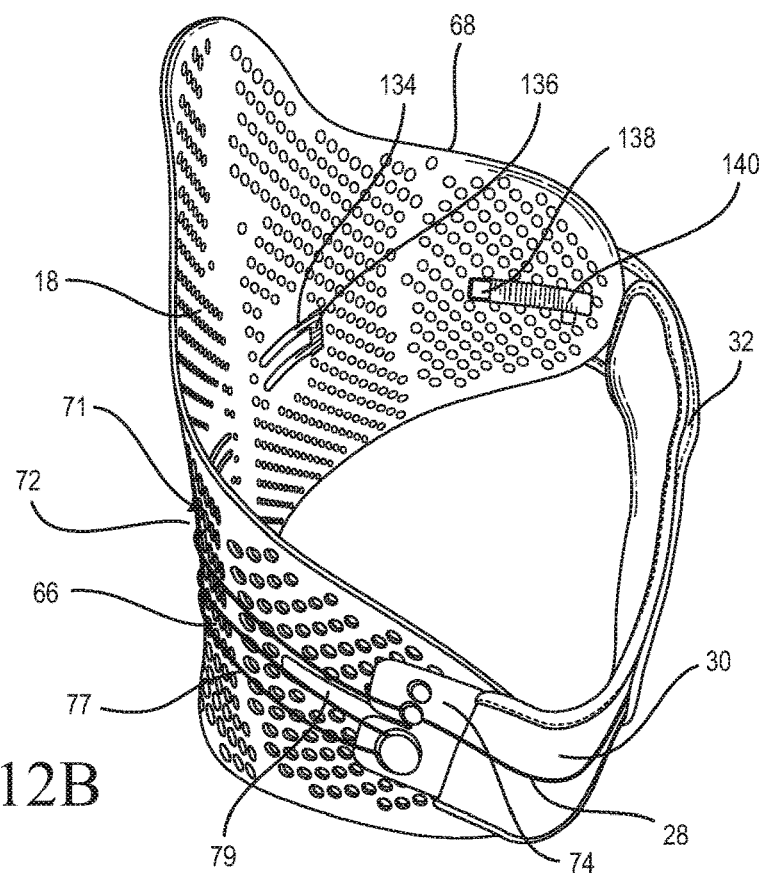
FIG. 12B is a schematic top view of the body interface of FIG. 2 having a belt tensioning system.
Figure 12C:
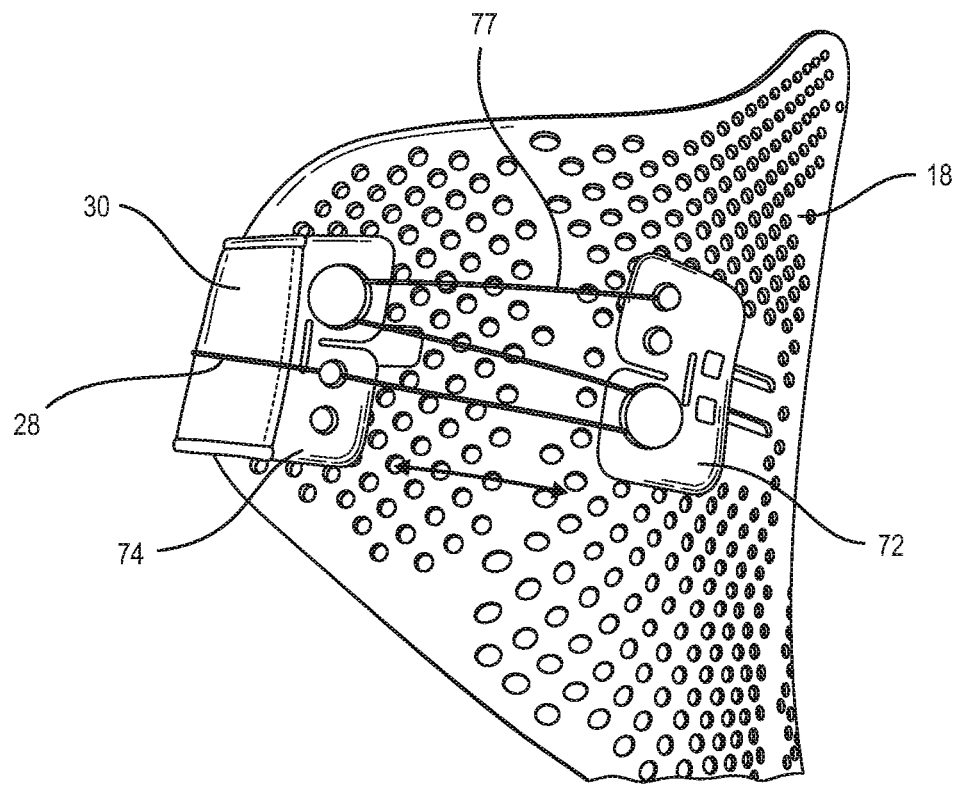
FIG. 12C is a schematic side view of the body interface of FIG. 2 having a belt tensioning system.

Referring to FIGS. 12A-12C, a closure device 71 for the attachment system 16 of FIG. 1A is on first and second lateral portions 66, 68 of panel 18. The closure device 71 includes first and second routing units 72, 73 fixedly attached on the first and second lateral portions 66, 68, respectively. The panel 18 defines at least one locking slot arrangement 134 in which an engaging part 136 of the first routing unit 72 locks to the panel 18 to prevent movement of the first routing unit 72 toward an end of the first lateral portion 66. The panel 18 defines an elongate slot 138 into which a slider part 140 of the first routing carriage 74 extends so the first routing carriage 74 is slidable relative to the panel 18 along the first lateral portion 66.

The closure units may be arranged with pulleys, as described in U.S. Pat. No. 8,172,779.

The arrangement of the closure device 71 with the elongate element 77 on the lateral portions 66, 68 allows for a full cinch function and leaves the posterior portion of the panel 18 free for attaching the hip assist mechanism 42 posteriorly. The hatched-out portions in FIGS. 12A-12C represent areas that can be removed from the panel to open to a frame as needed. The narrow regions remain horizontally on the lateral sides to form the track 79, which the routing units 72, 73 ride in.

The opposing first closure units are stationary and located more to midline posteriorly. When the tensioning elements are drawn, the closure units will draw the belt arms medially back inside the channels of the arms. The lordosis control can span across the frame laterally, so it has good purchase to rigid members on both sides.

Panel 18 may define zones and patterns of apertures 99. Apertures 99 may be grouped into lateral zones 103, 105 at lateral regions and a central zone 107. Zones 103, 105, 107 may be discretized by a column 115 wherein apertures are not defined, adding rigidity at desired locations. Within zones 103, 105, 107, discrete patterns 101 may be provided to facilitate anisotropic flexibility in desired directions; for instance, the apertures within lateral zones 103, 105 may be configured to facilitate circumferential bending of the panel 18 to allow an optimal amount of cooperation between an exoskeleton and the user. In central zone 107, the apertures may be configured to facilitate a more limited degree of circumferential bending and more longitudinal bending.

It is to be understood that not necessarily all objects or advantages may be achieved under any embodiment of the disclosure. Those skilled in the art will recognize that the body interface may be embodied or carried out in a manner that achieves or optimizes one advantage or group of advantages as taught without achieving other objects or advantages as taught or suggested herein.

The skilled artisan will recognize the interchangeability of various disclosed features. Besides the variations described herein, other known equivalents for each feature can be mixed and matched by one of ordinary skill in this art to construct a body interface under principles of the present disclosure. It will be understood by the skilled artisan that the features described herein may be adapted to orthopedic devices. Hence, this disclosure and the embodiments and variations thereof are not limited to a body interface but can be utilized in any orthopedic device.

Although this disclosure describes certain exemplary embodiments and examples of a body interface, it therefore will be understood by those skilled in the art that the present disclosure extends beyond the specifically disclosed embodiments to other alternative embodiments and/or uses of the disclosure and obvious modifications and equivalents thereof. It is intended that the present disclosure should not be limited by the particular disclosed embodiments described above, and may be extended to body interfaces and orthopedic devices, and other applications that may employ the features described herein.

The invention claimed is:

1. A body interface, comprising:
   a panel being semi-rigid or rigid, the panel arranged to control sagittal movement and control coronal movement to control spinal/hip motion of lateral bending and abduction, respectively, the panel arranged to control flexion-extension such that the panel is arranged with a superior or thoracic portion, an inferior or sacral portion, and a central or lumbar portion located between the superior portion and the inferior portion of the panel;
   a lumbar support anchored to the panel at an anchor point, and tensionable over and spaced a distance apart from the panel; and
   first and second arms located on opposed lateral sides of the panel through which first and second belt segments of an attachment system, respectively, extend to engage one another and to define a circumference around a user, the attachment system tensionable by at least one tensioning element;
   wherein the first and second arms each define a channel through which the first and second belt segments extend, the first and second arms each including a plate having a generally predetermined straight profile, the first and second arms are arranged to bend to a curved profile due to exertion of a load and returning to the generally predetermined straight profile upon release of the load;
   wherein the first and second arms define inner and outer surface layers comprising inner and outer textiles and a top layer spanning between the inner and outer surface layers, such that the top layer is more elastic than the inner and outer surface layers.

2. The body interface of claim 1, arranged to connect to an assistive system movable relative to the panel, and a driving system adapted to drive the assistive system.

3. The body interface of claim 2, wherein the assistive system includes a leg/hip assist mechanism and a leg connection, the leg/hip assist mechanism located on lateral sides of the panel.

4. The body interface of claim 3, wherein the driving system is located on a posterior side of the panel and includes a driving mechanism for moving the leg/hip mechanism.

5. The body interface of claim 1, wherein the lumbar support is flexible relative to the panel.

6. The body interface of claim 1, wherein the lumbar support is tensionable relative to the panel by a tensioning device.

7. The body interface of claim 1, wherein the inner and outer surface layers are substantially inelastic.

8. The body interface of claim 1, further comprising a padding layer extending along the plate and between the plate and the outer surface layer of the first and second arms.

9. The body interface of claim 8, wherein a lateral portion end of the panel overlaps the plate, the first and second belt segments being adapted to slide within the channel, while the first and second arms maintains their shape without interfering with the sliding of the first and second belt segments.

10. An exoskeleton comprising:
    a body interface arranged to stabilize on a user's muscle and soft-tissue, while remaining stable in position on a user according to relative movement of an assistive system attachable to the body interface;
    a panel being semi-rigid or rigid, the panel arranged to control sagittal movement and control coronal movement to control spinal/hip motion of lateral bending and abduction respectively, the panel arranged to control flexion-extension such that the panel is arranged with a superior or thoracic portion, an inferior or sacral portion, and a central or lumbar portion located between a superior portion and an inferior portion;
    a lumbar support attached to the panel at an anchor point;
    wherein the body interface further comprises first and second arms located on opposed lateral sides of the panel through which first and second belt segments of an attachment system, respectively, extend to engage one another and to define a circumference around the user, the attachment system tensionable by at least one tensioning element;
    wherein the first and second arms define elastic upper portions cooperating with inelastic inner and outer layers to permit flexure of the first and second arms.

11. The exoskeleton of claim 10, wherein the lumbar support is flexible relative to the panel.

12. The exoskeleton of claim 11, wherein the body interface further comprises a cover extending over the lumbar support and located between the cover and the panel.

13. The exoskeleton of claim 10, wherein the lumbar support further comprises a tensioning device for regulating tension in the lumbar support, where the tensioning device includes a cable extending through the first and second arms to engage the lumbar support.

14. A body interface, comprising:
    a panel comprising first and second lateral portions extending from a central portion;
    a lumbar support attached to the panel at superior and inferior attachment points, and tensionable relative to the panel; and
    at least one tensioning element;
    wherein the lumbar support comprises a first band having superior and inferior portions secured to superior and inferior ends of the panel, the first band tensioned between the superior and inferior ends so as to be spaced apart a clearance from the panel between such superior and inferior ends, the clearance being greatest at a center portion of the first band between the superior and inferior portions;

wherein the lumbar support comprises a second band having first and second portions secured to first and second lateral ends of the panel, the second band is spaced apart by a clearance from the panel between such first and second lateral ends, the clearance being greatest at a center portion of the second band between the first and second lateral ends.

15. The body interface of claim 14, a tensioning device is arranged to permit regulation of the at least one tensioning element to move an end of the lumbar support relative to the panel.

16. The body interface of claim 14, wherein the lumbar support has first and second lateral portions coupled to first and second tensioning devices each arranged to draw the first and second lateral portions in opposed directions relative to one another.

17. The body interface of claim 14, wherein the lumbar support is more flexible than the panel, the lumbar support being formed of breathable material and defining a clearance between the lumbar support and the panel, the clearance defining longitudinal and circumferential arcs or curvatures conforming to a user.

18. The body interface of claim 17, wherein the panel defines patterns of apertures configured to cooperate with the lumbar support to define longitudinal and circumferential arcs and to adjust the clearance between the lumbar support and the panel based on a degree of tensioning applied to the body interface.

\* \* \* \* \*